United States Patent [19]

Meguro et al.

[11] Patent Number: 5,362,742
[45] Date of Patent: Nov. 8, 1994

[54] QUINOLINE DERIVATIVES, THEIR PRODUCTION AND USE AS ACAT INHIBITORS

[75] Inventors: Kanji Meguro, Nishinomiya; Hitoshi Ikeda, Higashiosaka, both of Japan

[73] Assignee: Takeda Chemical Industries, Ltd., Japan

[21] Appl. No.: 646,735

[22] PCT Filed: Dec. 10, 1990

[86] PCT No.: PCT/JP90/01617
§ 371 Date: Feb. 1, 1991
§ 102(e) Date: Feb. 1, 1991

[87] PCT Pub. No.: WO91/09017
PCT Pub. Date: Jun. 27, 1991

[30] Foreign Application Priority Data

Dec. 11, 1989 [JP] Japan .................. 1-322172

[51] Int. Cl.⁵ .................. A61K 31/47; C07D 215/38
[52] U.S. Cl. .................. 514/312; 514/313; 546/153; 546/159
[58] Field of Search .................. 546/159, 153, 159; 514/312, 313

[56] References Cited

U.S. PATENT DOCUMENTS 3,798,226  3/1974  Meguro .................. 514/925

Primary Examiner—Cecilia Tsang
Assistant Examiner—Matthew V. Grumbling
Attorney, Agent, or Firm—Wegner, Cantor, Mueller & Player

[57] ABSTRACT

A quinoline derivative of the formula (I):

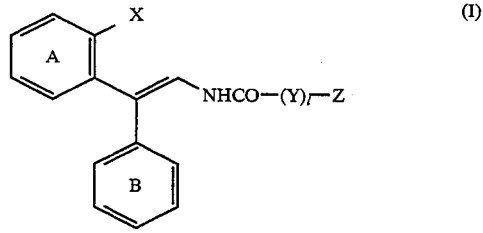

wherein each phenyl ring of A and B can have one or more substituents; X is

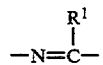

($R^1$ is a hydrogen atom, a lower alkyl group or a lower alkoxy group) or

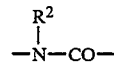

($R^2$ is a hydrogen atom or a lower alkyl group); Y is $-(CH_2)_m-$ (m is 0, 1 or 2) or $-CH=CH-$, Z is a group of the formula:

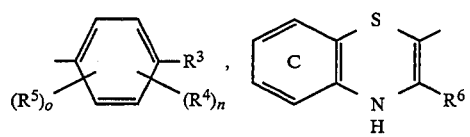

or

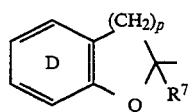

wherein each phenyl ring of C and D can have one or more substituents, $R^3$ and $R^4$ are each a hydrogen or halogen atom, or a lower alkyl, lower alkoxy, lower acyloxy, lower alkoxycarbonyloxy, N,N-di-lower alkylcarbamoyloxy, optionally esterified carboxy or hydroxyl group, $R^5$ is a halogen atom, or a lower alkyl, lower alkoxy, lower acyloxy, lower alkoxycarbonyloxy, N,N-di-lower alkylcarbamoyloxy, optionally esterified carboxy or hydroxyl group, $R^6$ and $R^7$ are each a hydrogen atom or a lower alkyl group, and n, o and p are each 1 or 2; l is 0 or 1; or its salt, which is useful as a drug for atherosclerosis.

4 Claims No Drawings

QUINOLINE DERIVATIVES, THEIR PRODUCTION AND USE AS ACAT INHIBITORS

BACKGROUND OF THE INVENTION

1. Field of the Invention

This invention relates to novel quinoline derivatives, their production and use. The compounds of this invention possess excellent inhibitory action against acyl-CoA: cholesterol acyltransferase (ACAT). Especially, the compounds of this invention inhibit the absorption of cholesterol through the intestinal tract of a mammal and also restrain the accumulation of cholesterol ester at the arterial wall, and accordingly are useful as a drug for preventing and treating hypercholesterolemia, atherosclerosis and various diseases caused thereby (e.g., ischemic cardiac diseases such as myocardial infarction, cerebrovascular disturbance such as cerebral infarction, cerebral apoplexy, etc.).

2. Description of the Prior Art

U.S. Pat. No. 3,798,226 mentions specifically 6-chloro-4-phenyl-3-phenylacetamidoquinoline (Compound A), and 6-chloro-3-(p-chlorophenylacetamido)-4-phenylquinoline (Compound B), which possess antitrichomonas or antiulcer action.

There has not been any report that the above mentioned compounds possess pharmacological activity useful as a drug for arteriosclerosis such as ACAT inhibitory activity and blood cholesterol lowering activity, and these points have not been studied so far.

Therefore, it has not been known that the compounds A and B and their analogue compounds are useful as a drug for atherosclerosis.

SUMMARY OF THE INVENTION

The inventors of this invention studied the physiological activities of the above mentioned compounds A and B and their analogue compounds, and found that new compounds which are not described concretely in the above mentioned publications, possess potent ACAT inhibitory activity and are useful as a drug for atherosclerosis.

Thus, this invention relates to (1) a quinoline derivative of the formula (I):

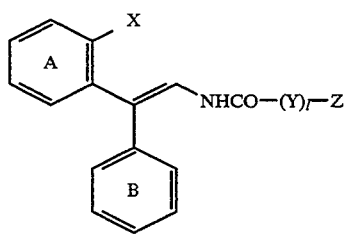

wherein each phenyl ring of A and B can have one or more substituents; X is

($R^1$ is a hydrogen atom, a lower alkyl group or a lower alkoxy group) or $$-N-CO-$$
$$\phantom{-N}|\phantom{CO}$$
$$\phantom{-N-}R^2$$

($R^2$ is a hydrogen atom or a lower alkyl group); Y is $-(CH2)_m-$ (m is 0, 1 or 2) or $-CH=CH-$, Z is a group of the formula:

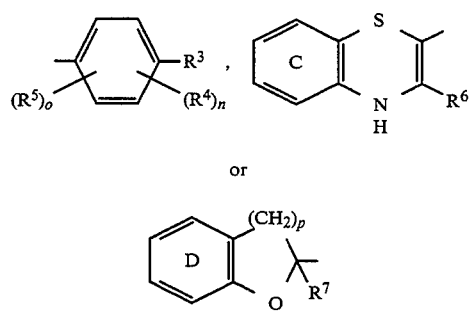

wherein each ring of C and D can have one or more substituents, $R^3$ and $R^4$ are each a hydrogen atom, a halogen atom, or a lower alkyl, lower alkoxy, lower acyloxy, lower alkoxycarbonyloxy, N,N-di-lower alkylcarbamoyloxy, optionally esterified carboxy or hydroxyl group, $R^5$ is a halogen atom, or a lower alkyl, lower alkoxy, lower acyloxy, lower alkoxycarbonyloxy, N,N-di lower alkylcarbamoyloxy, optionally esterified carboxy or hydroxyl group, $R^6$ and $R^7$ are each a hydrogen atom, or a lower alkyl group, and n, o and p are each 1 or 2; l is 0 or 1; or its salt;

(2) an ACAT inhibitory composition comprising a quinoline derivative of the formula (I), or its salt.

DESCRIPTION OF THE PREFERRED EMBODIMENT

Examples of the halogen atoms represented by $R^3$, $R^4$ and $R^5$ in the formula (I) are fluorine, chlorine, bromine or iodine atom, preferably fluorine atom.

Preferably, the lower alkyl groups for $R^1$, $R^2$, $R^3$, $R^4$, $R^5$, $R^6$ and $R^7$ are straight or branched chain ones having 1-6 carbon atoms, such as methyl, ethyl, propyl, isopropyl, butyl, isobutyl, sec-butyl, tert-butyl, pentyl, isopentyl, neo-pentyl, hexyl and the like.

Preferably, the lower alkoxy groups for $R^2$, $R^4$ and $R^5$ are straight or branched chain ones having 1-6 carbon atoms, such as methoxy, ethoxy, propoxy, isopropoxy, butoxy, isobutoxy, sec-butoxy, tert-butoxy, pentyloxy, isopentyloxy, neopentyloxy and hexyloxy.

The preferable lower acyloxy groups for $R^3$, $R^4$ and $R^5$ are straight or branched chain ones having 1-6 carbon atoms, such as formyloxy, acetoxy, propionyloxy, isobutyloxy, butyryloxy, isobutyryloxy, valeryloxy, isovaleryloxy, pivaloyloxy, hexanoyloxy and the like.

The preferable lower alkoxycarbonyloxy groups for $R^3$, $R^4$ and $R^5$ are ones containing straight or branched chain alkyl groups having 1-6 carbon atoms, such as methoxycarbonyloxy, ethoxycarbonyloxy, propoxycarbonyloxy, isopropoxycarbonyloxy, butoxycarbonyloxy, isobutoxycarbonyloxy, sec-butoxycarbonyloxy, tert-butoxycarbonyloxy, pentyloxycarbonyloxy, isopentyloxycarbonyloxy, neopentyloxycarbonyloxy, hexyloxycarbonyloxy, or the like.

The preferable N,N-di lower alkylcarbamoyloxy groups for $R^3$, $R^4$ and $R^5$ are ones containing straight or branched chain alkyl groups having 1-6 carbon atoms which may be the same or different. Examples of the N,N-di-lower alkylcarbamoyloxy groups are N,N-dimethylcarbamoyloxy, N,N-diethylcarbamoyloxy, N-methyl-N-ethylcarbamoyloxy, N,N-dipropylcarbamoyloxy, N,N-diisopropylcarbamoyloxy, N,N-dibutylcarbamoyloxy, N-methyl-N-propylcarbamoyloxy, N-ethyl-N-propylcarbamoyloxy, N,N-di-sec-butylcarbamoyloxy, N,N-di-tert-butylcarbamoyloxy, N,N-dipentylcarbamoyloxy, N,N-diisopentylcarbamoyloxy, N,N-dineopentylcarbamoyloxy, N,N-dihexylcarbamoyloxy, or the like.

The preferable optionally esterified carboxy groups for $R^3$, $R^4$ and $R^5$ are a carboxyl group and carboxy groups esterified by an alkyl of 1–6 carbon atoms such as methyl., ethyl, propyl, isopropyl, butyl, isobutyl, sec-butyl, tert-butyl, pentyl or hexyl.

The phenyl group shown by the formula

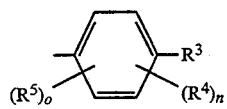

(the symbols have the same meanings as defined above) may possesses one to five substituents, preferably two to four substituents, which may be the same or different. Also, an interesting group is a phenyl group of the formula

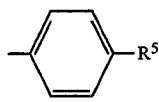

wherein $R^5$ has the same meaning as defined above.

Each of the A, B, C and D rings can have one or more substituents. Examples of the substituents are a halogen atom, an optionally halogenated lower alkyl group, an optionally halogenated lower alkoxy group, an optionally halogenated lower alkylthio group, nitro group, an optionally esterified carboxy group, hydroxyl group, a $C_{1-4}$ acyloxy (e.g., formyloxy, acetoxy, propionyloxy, etc.) and a $C_{1-3}$ acyl group (e.g., formyl, acetyl, propionyl, etc.). The halogen atom in these groups may be a fluorine, chlorine, bromine or iodine atom.

The optionally halogenated lower alkyl groups include the above mentioned lower alkyl groups and these lower alkyl groups substituted with one to five halogen atoms, such as methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, 2-trifluoromethylethyl, butyl, 4,4,4-trifluorobutyl, isobutyl, sec-butyl, tert-butyl, pentyl, isopentyl, neopentyl, 5,5,5-trifluoropentyl, 4-trifluoromethylbutyl, hexyl, 6,6,6-trifluorohexyl or 5-trifluoromethylpentyl.

The optionally halogenated lower alkoxy groups and the optionally halogenated lower alkylthio groups can be those formed by the combination of the above mentioned lower alkyl groups or halogenated lower alkyl groups and an oxygen atom or a sulfur atom.

The optionally esterified carboxy groups may be a carboxyl group and carboxy groups esterified by an alkyl of 1–6 carbon atoms such as methyl, ethyl, propyl, isopropyl, butyl, isobutyl, sec-butyl, tert-butyl, pentyl or hexyl.

The substituent(s) on the rings A, B, C and D can be at any position of each ring, and these substituents may be the same or different, and the number of the substituent(s) may be 1 to 4. The preferred position(s) of the substituent(s) are 6-, 7- and/or 8- positions of the quinoline nucleus for the ring A, and 2- position for the ring B.

The compounds of the formula (I) can form their salts with acids (e.g., inorganic acids such as hydrochloric acid, hydrobromic acid, sulfuric acid and phosphoric acid; organic acids such as methanesulfonic acid, fumaric acid, maleic acid, citric acid and tartaric acid); and also can form their salts with alkali metals or alkaline earth metals (e.g., sodium, potassium or calcium salt) in case where they contain an acid group such as a carboxyl group.

The quinoline derivative of the formula (I) and its salt can be prepared, for example, by reacting a compound of the formula (II):

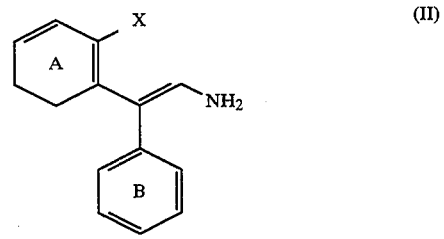

or its salt with a compound of the formula (III):

Z—(Y)$_l$—COOH (III)

or its reactive derivative, wherein the symbols used therein have the same meanings as defined above.

The compound (I) wherein Y is —CH=CH—, if required, is further reduced to make the corresponding compound (I) wherein Y is —CH$_2$CH$_2$—.

When Z is of the following formula:

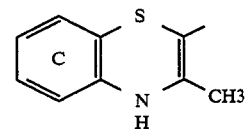

and l is 0, the quinoline derivative of the formula (I) and its salt can also be prepared by reacting the compound (II) or its salt with diketene to obtain a compound of the formula (IV):

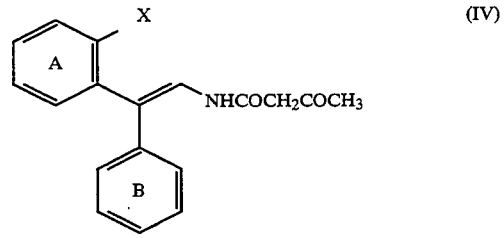

[wherein the symbols used therein have the same meanings as defined above].

and then reacting the compound (IV) with a compound of the formula (V):

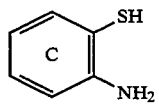

(V)

[wherein the symbols used therein have the same meanings as defined above].

(1) In the case of reacting the compound (II) or its salt with the compound (III), it is preferable that a suitable condensing agent is used or the compound (III) is led to its reactive derivative before reacting with the compound (II). Examples of such condensing agents are dicyclohexylcarbodiimide (DCC), diethylphosphoryl cyanide (DEPC), diphenylphosphoryl azide (DPPA) or the like. When such a condensing agent is used, the reaction is usually carried out in a solvent (e.g., tetrahydrofuran, dioxane, dimethoxyethane, ethyl acetate, benzene, toluene, N,N-dimethylformamide, dimethylsulfoxide) at about $-10°$ C.$\sim 100°$ C., preferably at about $0°$ C.$\sim 60°$ C., optionally in the presence of a base. The amount of each of the compound (III) and the condensing agent to be used is about 1-5 equivalents, preferably about 1-3 equivalents, to the compound (II). Examples of the bases to be used are triethylamine, N-methylmorpholine, pyridine or the like. The amount of the base is about 1-5 equivalents, preferably 1-3 equivalents, to the compound (II).

Examples of the reactive derivatives are the acid halide (e.g., chloride, bromide), acid anhydride, mixed acid anhydride (e.g., anhydride with methyl carbonate, anhydride with ethyl carbonate, anhydride with isobuthyl carbonate or the like), active ester (e.g., ester with hydroxy succinimide, ester with 1-hydroxybenzotriazole, ester with N-hydroxy-5-norbornene-2,3-dicarboxyimide, ester with p-nitrophenol, ester with 8-oxyquinoline or the like). Especially, the acid halide is more preferable.

The reaction of the compound (II) or its salt with the reactive derivative is usually carried out in a solvent (e.g., chloroform, dichloromethane, diethyl ether, tetrahydrofuran, dioxane, dimethoxyethane, ethyl acetate, benzene, toluene, pyridine, N,N-dimethylformamide or the like) at about $-10°$ C.$\sim 120°$ C., preferably about $0°$ C.$\sim 100°$ C., optionally in the presence of a base. The amount of the reactive derivative to be used is about 1-5 equivalents, preferably about 1-3 equivalents, to the compound (II). Examples of the bases to be used are triethylamine, N-methylmorpholine, pyridine, sodium carbonate, potassium carbonate, sodium hydrogen carbonate or the like. The amount of the base is about 1-5 equivalents, preferably 1-3 equivalents, to the compound (II). In the case where a solvent immiscible with water is used, the reaction may be carried out by adding water in a two-layer system.

The compound (I) having $-CH=CH-$ as Y can be converted by reduction to the compound having $-CH_2CH_2-$ as Y.

Usable reducing agents are lithium aluminum hydride, sodium borohydride, lithium borohydride, and the like. The amount of the reducing agent is about 0.5-5 equivalents, preferably 0.5-2 equivalents. The reaction is usually carried out in a solvent (e.g., methanol, ethanol, ethyl ether, tetrahydrofuran, dioxane or the like) at about $-5°$ C. $\sim 120°$ C., preferably $0°$ C.$\sim 100°$ C.

The reduction may be conducted by using a metal and an acid or a metal and a base, instead of using the aforesaid reducing agents. When a metal such as zinc, tin, iron or the like is used, an acid (e.g., hydrochloric acid, sulfuric acid, acetic acid or the like) is mainly employed as a hydrogen supplying source, while a base (e.g., ammonia, ethylamine, dimethylamine, ethylamine, diethylamine or the like) is mainly employed as a hydrogen supplying source when a metal of potassium, sodium, lithium or the like is used. The amount of the metal to be used in the reduction is about 1-10 equivalents, preferably 1-5 equivalents. The reduction is usually carried out in a solvent (e.g., an alcohol such as methanol, ethanol or the like, or an ether such as tetrahydrofuran, dioxane, dimethoxyethane, or the like). The acid or base used for the reduction may be employed as a solvent. The temperature for reduction is about $0°$ C.$\sim 120°$ C., preferably $0°$ C.$\sim 80°$ C.

The aforesaid reduction may be a catalytic reduction using a catalyst. Examples of the catalysts to be used are palladium black, palladium carbon, platinum oxide, platinum black, Raney nickel, rhodium carbon or the like. The catalytic reduction is usually carried out in a solvent (e.g., methanol, ethanol, isopropanol, tetrahydrofuran, dioxane, dimethoxyethane, formic acid, acetic acid, N,N-dimethylformamide or the like) under from atmospheric pressure to 20 atm., preferably from atmospheric pressure to 5 atm. The temperature for the catalytic reduction is about $0°$ C. $\sim 100°$ C., preferably about $0°$ C.$\sim 80°$ C.

(2) The reaction of the compound (II) with diketene is usually conducted in a solvent (e.g., benzene, toluene or the like) at about $20°$ C. $\sim 120°$ C., preferably about $50°$ C.$\sim 100°$ C., optionally in the presence of a base (e.g., triethylamine, N-methylmorpholine, pyridine or the like). The amount of diketene to be used is about 1-2.0 equivalents, preferably about 1-1.2 equivalents, to the compound (II). The amount of the base to be used is about 0.01-1 equivalents, preferably about 0.05-0.5 equivalents, to the compound (II). The resulting acetoacetyl compound (IV) with or without isolation and purification can be reacted with the compound (V) to obtain the quinoline derivative (I) of the present invention. The compounds (IV) and (V) are heated for reaction in e.g., dimethylsulfoxide. The reaction temperature is about $90°$ C. $\sim 170°$ C., preferably about $110°$ C. $\sim 150°$ C. The amount of the compound (V) to be used is about 1-2 equivalents, preferably about 1-1.2 equivalents, to the compound (IV).

When the compound (I) prepared by the above method contains lower alkoxy group(s), such group(s), if required, can be converted into hydroxyl group(s) by the reaction with boron tribromide or the like. This reaction is usually carried out in a solvent (e.g., dichloromethane, chloroform, carbon tetrachloride, benzene, toluene, etc.), at about $-20°$ C. $\sim 80°$ C., preferably at about $0°$ C.$\sim 30°$ C. The amount of boron tribromide to be used is about 1-10 equivalents, preferably about 1-5 equivalents, to each lower alkoxy group.

The compound (I) which contains hydroxyl group(s) on its benzene ring can be converted, if required, into the corresponding one having alkoxy, acyloxy, alkoxycarbonyloxy or N,N-dialkylcarbamoyloxy group(s) upon alkylation, acylation, alkoxycarbonylation or N,N-dialkylcarbamoylation. The alkylation can be conducted by using an alkylating agent such as an optionally substituted alkane halide (e.g., chloride, bromide or iodide), or a sulfuric ester or sulfonic ester (e.g., methanesulfonate, p-toluenesulfonate or benzenesulfonate) in a solvent (e.g., methanol, ethanol, propanol, dimethoxyethane, dioxane, tetrahydrofuran, acetone, N,N-dimethylformamide or the like) in the presence of a base (e.g., potassium carbonate, sodium carbonate, potassium hydroxide, sodium hydroxide or the like). The reaction temperature may be usually about $-10°$ C.$\sim 100°$ C., preferably about $0°$ C.$\sim 80°$ C. The amount of the alkylating agent is about 1–2 equivalents, preferably about 1–1.5 equivalents, to the phenolic derivative.

The acylation can be conducted by using an appropriate carboxylic acid or its reactive derivative. The reaction varies with the kind of the reactive derivative or the kind of the phenolic derivative, but when the reactive derivative is used, the reaction is usually conducted in a solvent (e.g., benzene, toluene, ethyl ether, ethyl acetate, chloroform, dichloromethane, dioxane, tetrahydrofuran, N,N-dimethylformamide or pyridine), optionally in the presence of an appropriate base for accelerating the reaction (e.g., sodium hydrogen carbonate, potassium hydrogen carbonate, sodium carbonate, potassium carbonate, sodium acetate, triethylamine or pyridine). The reactive derivatives may be the acid anhydride, mixed acid anhydride or acid halide (e.g., chloride or bromide). The amount of the acylating agent to be used is about 1–10 equivalents, preferably about 1–5 equivalents, to the phenolic derivative. The reaction temperature is usually about $0°$ C.$\sim 150°$ C., preferably about $10°$ C.$\sim 100°$ C.

The alkoxycarbonylation can be carried out by the same manner as in the acylation with the use of alkoxycarbonyl halide (e.g., chloride, bromide).

The N,N-dialkylcarbamoylation can be conducted by the same manner as in the acylation or alkoxycarbonylation with the use of N,N-dialkylcarbamoyl halide (e.g., chloride, bromide). The reaction may be performed in the presence of N,N-dimethylaniline, 4-(N,N-dimethylamino)pyridine or the like for accelerating the reaction.

When the compound (I) prepared by the above method contains an esterified carboxy or acyloxy group, such group if required can be converted into a carboxy or hydroxyl group, respectively, upon hydrolysis. The hydrolysis can usually be conducted by using an alkali metal or alkaline earth metal hydroxide such as sodium hydroxide, potassium hydroxide or barium hydroxide in the presence of a solvent (e.g., an alcohol such as methanol, ethanol or propanol, or the like). The reaction temperature is about $0°$ C.$\sim 100°$ C., preferably about $20°$ C.$\sim 80°$ C.

The object compounds (I) obtained in the above methods can be isolated and purified by a known method for isolation and purification (e.g., concentration, extraction by solvent, column chromatography, recrystallization, etc.)

The salt of the compound (I) may be formed by a known method when the compound (I) having a basic nitrogen atom is in the free form and/or contains an acid radical present in its molecule in the free form. The aforesaid compound (I) obtained in the salt form may be converted into the free form by a known method.

The compounds (I) possess excellent inhibitory action against acyl-CoA: cholesterol-acyltransferase (ACAT), and their acute toxicity and toxicity by repeated administration are low.

It is known that ACAT is an enzyme relating to the esterification of cholesterol with higher fatty acids in cells, and plays an important role in the absorption of cholesterol through the small intestine and accumulation of cholesterol ester in the cells. Accordingly, ACAT inhibitors can inhibit the absorption of dietary cholesterol through the intestinal tract, restrain the rise of blood cholesterol level, restrain the accumulation of cholesterol ester in the cells at the atherosclerotic lesion and therefore prevent the progress of atherosclerosis.

The compounds (I) of the present invention are useful as a safe drug for preventing and treating hypercholesterolemia, atherosclerosis and diseases caused thereby (e.g., ischemic cardiac diseases such as myocardial infarction, cerebrovascular disturbances such as cerebral infarction, cerebral apoplexy, etc.) in mammals (e.g., mouse, rat, hamster, rabbit, cat, dog, horse, cattle, sheep, monkey, human, etc.).

The compound (I) may exhibit lipoperoxide inhibitory action (antioxidizing action). It is known that a hyperoxidation of a lipid in the organism is related to arteriosclerosis or crisis of ischemic cardiac diseases in the brain or cardiovascular system. Accordingly, the compounds (I) having both of ACAT inhibitory action and antioxidizing action can prevent and treat various diseases in blood vessels caused by blood cholesterol and lipoperoxide, resulting in that the compounds (I) are highly useful as a drug.

The compounds (I), when used as a drug, are mixed with a pharmaceutically acceptable carrier, diluent or excipient to form powders, granules, tablets, capsules or injections for oral preparations or parenteral preparations. The compound (I) is preferably administered orally when it is used for the purpose of inhibiting the absorption of cholesterol. Dosage of the compound (I) depends on the kind of the compound, administration route, condition and age of the patient, etc. For example, when a compound (I) is administered orally to an adult patient having hypercholesterolemia, a daily dose of about 0.005–50 mg, preferably about 0.05–10 mg, more preferably about 0.2–4 mg of the compound is administered per 1 kg of weight of the patient, preferably divided into 1–3 times.

The quinoline compounds (II) as the starting materials for the compounds (I) can be prepared by methods known in the art but may be industrially advantageously prepared e.g., by the following methods.

[Method A]

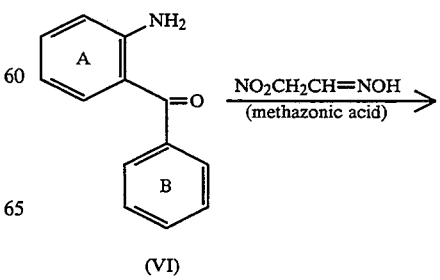

(VI)

-continued

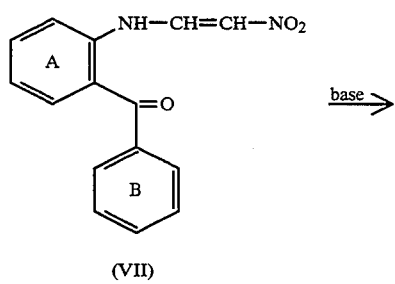

(VII)

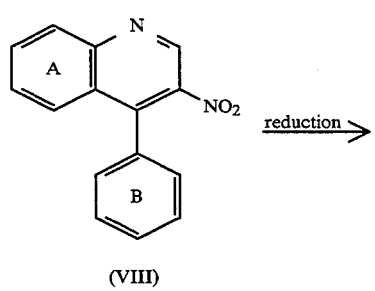

(VIII)

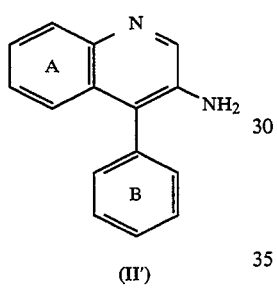

(II')

[The symbols have the same meanings as defined above.]

[Method B]

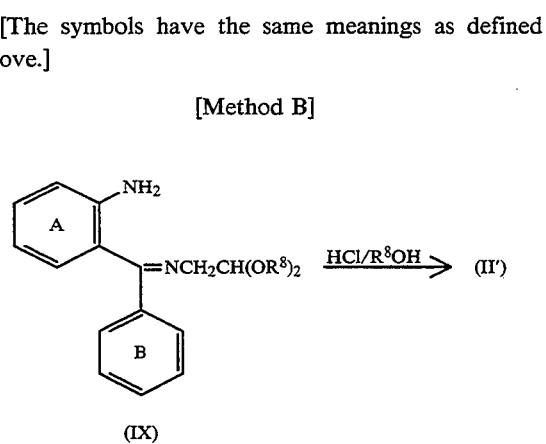

(IX)

[In the formula, $R^8$ is a lower alkyl and the other symbols have the same meanings as defined above.]

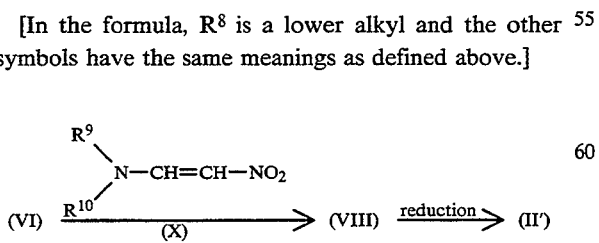

[$R^9$ and $R^{10}$ are each the same or different lower alkyl, phenyl group or benzyl group, or are combined to form a ring with adjacent nitrogen atom.]

Method 10]

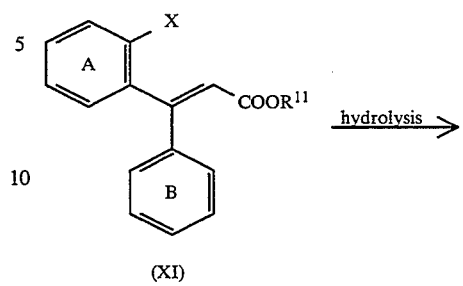

(XI)

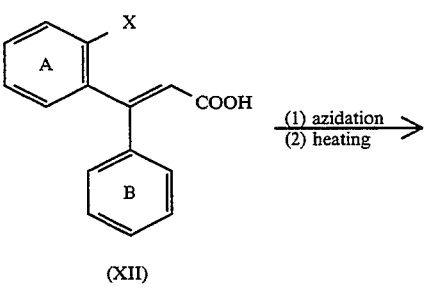

(XII)

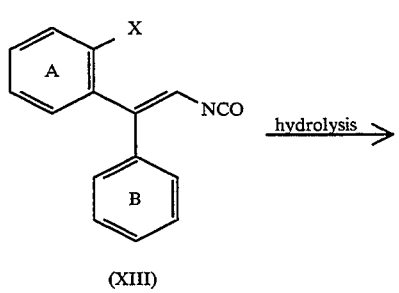

(XIII)

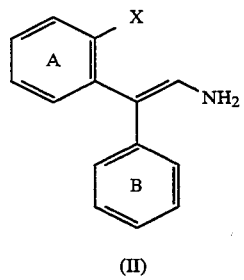

(II)

[In the formula, $R^{11}$ is a lower alkyl and the other symbols have the same meanings as defined above. ]

Method A]

The method for preparing the 3-aminoquinoline (II') by firstly reacting the 2-aminobenzophenone derivative (VI) via the compounds (VII) and (VIII) is disclosed in Journal of Chemical Society, pp.3914 (1953) or Japanese Examined Patent Application No. 6474/1973. Therefore, the 3-aminoquinoline (II') can be prepared by the above-mentioned method or methods analogous to said method.

[Method B]

The compound (II') can be prepared by the method disclosed in Japanese Examined Patent Application No. 6474/1973 or the Yakugakuzasshi, Vol.93, pp.1263(1973) or the methods analogous to said method.

[Method C]

Examples of the lower alkyl groups for $R^9$ and $R^{10}$ are ones having 1-4 carbon atoms, such as methyl, ethyl, propyl, isopropyl, butyl or the like. When $R^9$ and $R^{10}$ connect together to form a ring with a nitrogen atom, the resultant ring may contain another nitrogen or oxygen atom. Examples of said rings are 5-7 membered rings such as a pyrrolidine ring, piperidine ring, homopiperidine ring, morpholine ring or the like.

The reaction of the compound (VI) with the compound (X) is usually conducted in a solvent (e.g., ethyl acetate, acetone, benzene, toluene) in the presence of an acid (e.g., hydrochloric acid, hydrobromic acid, sulfuric acid, benzenesulfonic acid, p-toluenesulfonic acid, methanesulfonic acid). The aforesaid acid may be used in anhydrous state or as aqueous solution. The reaction may be carried out in the homogeneous system or in the two-layer system of water and solvent. The amount of the compound (X) to be used is about 1-10 mols, preferably about 2-6 mols, to 1 mol of the compound (VI). The amount of the acid to be used is about 1-20 mols, preferably about 2-10 mols, to 1 mol of the compound (VI). The reaction temperature is usually about 20° C.~100° C., preferably about 50° C.~80° C.

[Method D]

Examples of the lower alkyl groups for $R^{11}$ in the compound (XI) are ones having 1-5 carbon atoms, such as methyl, ethyl, propyl, isopropyl, butyl, isobutyl, sec-butyl or tert-butyl.

In the method, the quinoline-3-carboxylic acid ester (XI) is hydrolyzed to give the carboxylic acid (XII), which then is subjected to azidation and heating to convert into the 3-isocyanate derivative (XIII). The hydrolysis of the compound (XI) can be usually conducted by using an alkali metal or alkali earth metal hydroxide (e.g., sodium hydroxide, potassium hydroxide or barium hydroxide) in a solvent (e.g., alcohols such as methanol, ethanol and propanol, or ethers such as dioxane, tetrahydrofuran and dimethoxyethane). The reaction temperature is about 0° C.~100° C., preferably about 20° C.~80° C. The alkali is used in about 1-5 equivalents, to the compound (XI).

Any known methods for converting a carboxylic acid to an acid azide can be applied for the compound (XII). For example, the compound (XII) can be converted to the corresponding acid azide by using diphenylphosphoryl azide (DPPA) as an azidating agent. This reaction can be usually carried out in an inert solvent (e.g., ethers such as ethyl ether, isopropyl ether, dimethoxyethane, tetrahydrofuran and dioxane; aromatic hydrocarbons such as benzene, toluene and xylene; esters such as methyl acetate and ethyl acetate, ketones such as acetone and methyl ethyl ketone; or pyridine or N,N-dimethylformamide). The reaction may be conducted in the presence of a base (e.g., triethylamine, tributylamine or N-methylmorpholine). The reaction is usually carried out at about 0° C.~200° C., preferably at about 10° C.~100° C. The amount of DPPA to be used is usually about 1-2 equivalents, preferably about 1-1.5 equivalents, to the compound (XII). Thus produced acid azide is usually converted to the isocyanatoquinoline (XIII) without isolation by heating, although the acid azide can be isolated and purified by a conventional method. This conversion reaction is preferably carried out in a solvent used for the azidation. The conversion reaction is carried out under heating usually at about 60° C.~200° C., preferably at about 60° C.~150° C. The thus produced compound (XIII) can be isolated by a known method or used as the starting material for preparing the 3-aminoquinoline (II). That is, the compound (XIII) can be converted into the aminoquinoline (II) upon hydrolysis. The hydrolysis can be usually conducted by using an alkali (e.g., sodium hydroxide, potassium hydroxide or barium hydroxide) in a solvent (e.g., alcohols such as methanol, ethanol and propanol; ethers such as dioxane, tetrahydrofuran and dimethoxyethane; and other solvents mentioned in the azidation of the compound (XII)). The reaction temperature is about 0° C.~150° C., preferably about 10° C.~100° C., and the amount of the alkali to be used is about 1-5 equivalents, to the compound (XIII).

The compound (XI) can be prepared e.g., by the following methods.

[Method E]

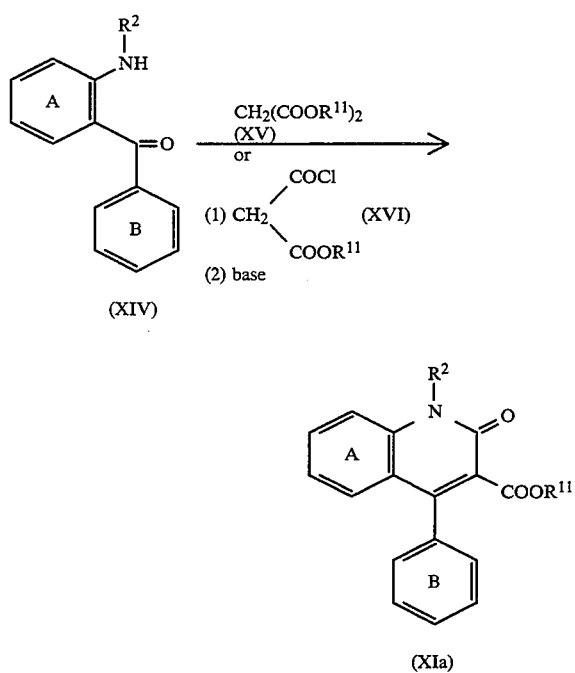

[The symbols have the same meanings as defined above.]

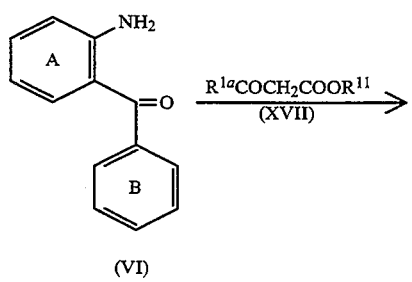

-continued

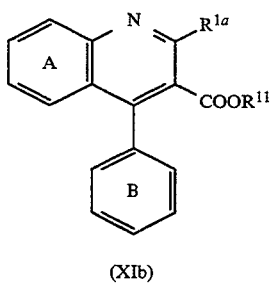

(XIb)

[$R^{1a}$ is a lower alkyl group and the other symbols have the same meanings as defined above.]

[Method G]

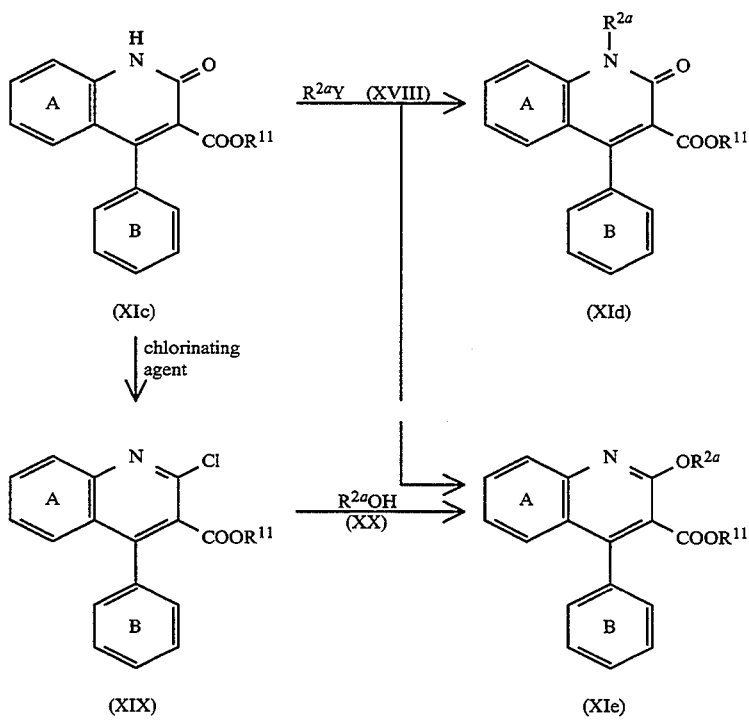

[$R^{2a}$ is a lower alkyl group, Y is a leaving group and the other symbols have the same meanings as defined above.]

[Method H]

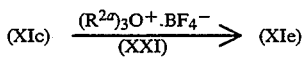

[$R^{2a}$ is as defined above.]

The lower alkyl groups mentioned in $R^{1a}$ and $R^{2a}$ are applicable to the lower alkyl groups for $R^1$ and $R^2$ of the above formulae. Examples of the leaving groups represented by Y are a halogen (e.g., chlorine, bromine or iodine), an alkylsulfonyloxy group (e.g., methanesulfonyloxy or ethanesulfonyloxy), an arylsulfonyloxy (e.g., benzenesulfonyloxy or p-toluenesulfonyloxy) or an alkoxysulfonyloxy group (e.g., methoxysulfonyloxy or ethoxysulfonyloxy).

[Method E]

The 2-aminobenzophenone derivative (XIV) is firstly reacted with the malonic acid diester (XV), or with the compound (XVI) followed by the reaction with a base, thereby affording the ring-closed product (XIa).

The reaction of the compound (XIV) with the compound (XV) to give the compound (XIa) is usually conducted under heating without any solvent, preferably in the presence of a base such as piperidine, pyrrolidine or triethylamine. The reaction temperature is usually about 100° C.~200° C., preferably about 130° C.~170° C. The amount of the compound (XV) to be used is about 1-5 equivalents, preferably about 1-3 equivalents, to the compound (XIV). The base is used in about 0.1-1 equivalent, to the compound (XIV).

The reaction of the compound (XIV) with the compound (XVI) is usually conducted in a solvent (e.g., ethers such as ethyl ether, dioxane, tetrahydrofuran and dimethoxyethane; esters such as methyl acetate and ethyl acetate; halogenated hydrocarbons such as dichloromethane and chloroform; aromatic hydrocarbons such as benzene and toluene; pyridine or dimethylformamide), optionally in the presence of a base (e.g., triethylamine, pyridine, potassium carbonate, sodium carbonate, potassium hydrogen carbonate or sodium hydrogen carbonate) and water. The amount of the compound (XVI) to be used is about 1-5 equivalents, preferably 1-2 equivalents, to the compound (XIV), and the amount of the base is about 1-5 equivalents, preferably about 1-2 equivalents, to the compound (XIV). The reaction temperature is usually about 0° C.~100° C., preferably about 0° C.~60° C. The reaction gives the compound (XXII);

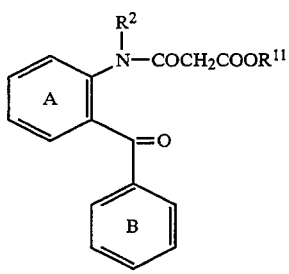

(XXII)

wherein the symbols are the same meanings as defined above. The compound (XXII) with or without isolation is reacted with a base to give the ring-closed product (XIa). The ring-closure reaction is usually conducted in a solvent (e.g., benzene, toluene, xylene, tetrahydrofuran, dioxane or dimethoxyethane). Examples of the bases are potassium t-butoxide, sodium methoxide, sodium ethoxide, piperidine, pyrrolidine, triethylamine, 1,5-diazabicyclo[4,3,0]non-5-en (DBN), 1,8-diazabicyclo[5,4,0]-7-undecene (DBU) and 1,4-diazabicyclo[2,2,2]octane (DABCO). The reaction temperature is usually about 0° C.~200° C., preferably about 20° C.~150° C., although it varies depending upon the kind of the base. The base is used in about 0.1-2 equivalents, preferably about 0.1-1.5 equivalents, to the compound (XI). The reaction is also conducted by removing the resulting water by use of Dean-Stark's apparatus, for acceleration purposes.

[Method F]

The method comprises reacting the compound (VI) with the acylacetic acid ester (XVII) to give the compound (XIb), The reaction is usually conducted in a solvent (e.g.., alcohols such as methanol, ethanol and propanol; ethers such as tetrahydrofuran, dioxane and dimethoxyethane; organic acids such as formic acid, acetic acid and propionic acid; dimethylformamide or dimethyl sulfoxide) in the presence of an acid catalyst (e.g., mineral acids such as hydrochloric acid, sulfuric acid and phosphoric acid; and sulfonic acids such as methanesulfonic acid, ethanesulfonic acid, camphorsulfonic acid, benzenesulfonic acid and toluenesulfonic acid). The reaction may be conducted without using solvent in the presence of the acid. The reaction temperature is usually about 10° C.~200° C., preferably about 20° C.~150° C. The amount of the compound (XVII) to be used is about 1-10 equivalents, preferably about 1-3 equivalents, to the compound (VI). The acid catalyst is usually used in about 0.001-2 equivalents, preferably about 0.01-1 equivalent, to the compound (VI).

[Method G]

The method involves the alkylation of the compound (XIc) with the compound (XVIII) to give the N-alkyl compound (XId) and/or O-alkyl compound (XIe). The reaction is usually conducted in a solvent (e.g., alcohols such as methanol and ethanol; ethers such as tetrahydrofuran, dioxane and dimethoxyethane; dimethylformamide or dimethyl sulfoxide) in the presence of a base (e.g., sodium hydroxide, potassium hydroxide, sodium methoxide, sodium ethoxide, potassium t-butoxide, sodium amide, potassium carbonate or sodium carbonate). As the procedure for this reaction, the base is added to a solution of the compound (XIc) to give the corresponding salt, which is then reacted with the compound (XVIII). Alternatively, the reaction can be conducted in such a way that the base and the compound (XVIII) are added simultaneously to the compound (XIc). Usually, the reaction product is a mixture of the compounds (XId) and (XIe), which can be separated by recrystallization or chromatography. Also, either one of the compounds (XId) and (XIe) may predominantly be produced, depending upon the kind of the compound (XIc) and reaction condition. The reaction temperature is usually about 0° C.~150° C., preferably about 10° C.~60° C. Each amount of the base and the compound (XVIII) to be used is usually about 1-3 equivalents, preferably 1-1.5 equivalents, to the compound (XIc).

Also, the compound (XIe) can be prepared by chlorinating the compound (XIc) with a chlorinating agent to obtain the compound (XIX) and reacting the resultant (XIX) with the alcohol (XX). Examples of the chlorinating agents for (XIc) are thionyl chloride, phosphorus oxychloride, phosphorus trichloride and phosphorus pentachloride, among which phosphorus oxychloride is preferable. The chlorination is usually conducted under heating to about 50° C.~150° C., preferably about 70° C.~120° C. without any solvent. However, it can be conducted in an inert solvent (e.g., chloroform, benzene, toluene and xylene) and in the presence of pyridine, N,N-dimethylformamide or the like which can accelerate the reaction, if required. The amount of the chlorinating agent to be used is usually about 1-50 equivalents, preferably 1-20 equivalents to the compound (XIc). The resulting product (XIX) can be isolated and purified but can be directly used to react with the compound (XX) to afford the compound (XIe). The reaction of the compound (XIX) with the compound (XX) is preferably conducted in the presence of a base (e.g., an alkoxide of $R^{2a}OH$ with a metal). Examples of the metals to form such alkoxide are sodium or potassium. The amount of the metal alkoxide to be used is usually about 1-5 equivalents, preferably about 1-3 equivalents to the compound (XIX). The reaction temperature is usually about 20° C.~20° C., preferably about 50° C.~100° C. Also, the compound (XX) itself can be preferably used as the solvent.

[Method H]

In this method, the compound (XIe) can be prepared by reacting the compound (XIc) with the trialkyloxonium fluoroborate (XXI). The reaction is usually conducted in a solvent (e.g., dichloromethane or chloroform) at about 0° C.~60° C., preferably about 15° C.~40° C. The compound (XXI) is usually used in about 1-10 moles, preferably about 1-3 moles to the compound (XIc).

Activity

Pharmacological test results on the compounds (I) and their salts of the present invention are shown in the following.

1. Acyl-CoA: cholesterol acyltransferase (ACAT) inhibitory activity

[Methods]

The enzyme ACAT was prepared by the method of Heider et.al., described in Journal of Lipid Research, Vol. 24, page 1127 (1982), from the mucosal microsome fraction of the small intestine of male, 6-week old Sprague-Dawley rats which had been fasted for 20 hours.

ACAT activity was calculated by the method of Helgerud et. al. described in Journal of Lipid Research, Vol. 22, page 271 (1981), namely, by measuring the amount of the labeled cholesterol ester produced from [1-$^{14}$C] oleoyl-CoA and endogenous cholesterol.

[Results]

Inhibition rates (%) of the production of the labeled cholesterol ester wherein $10^{-6}$M of test compounds were added are shown as an index of ACAT inhibitory activity in Table 1.

TABLE 1

| Test Compound (Example No.) | ACAT Inhibition Rate (%) |
|---|---|
| 1 | 82.2 |
| 3 | 83.4 |
| 4 | 84.8 |
| 6 | 79.3 |
| 8 | 62.0 |
| 11 | 94.3 |
| 12 | 41.2 |
| 13 | 64.7 |
| 14 | 83.1 |
| 15 | 76.0 |
| 16 | 72.6 |
| 18 | 94.0 |
| 22 | 92.6 |
| 23 | 65.9 |
| 24 | 69.4 |
| 25 | 73.7 |
| 27 | 83.7 |
| 32 | 66.6 |
| 33 | 81.7 |
| 34 | 86.4 |
| 35 | 81.7 |
| 36 | 63.0 |
| 38 | 78.2 |
| 43 | 97.0 |
| 46 | 72.6 |

2. Lipoperoxide inhibitory activity

[Method]

From 10-week, old, male Sprague-Dawely rats which were fed CE-2 diet (Nippon Claire) and water, their brains were taken out by the method of Stocks disclosed in Clinical Science Molecular Medicine, Vol. 78, page 215 (1974), to form lipoperoxide by natural oxidation. The compound (I) in an amount of $10^{-3}$ moles was dissolved in ethanol, and the resultant (10 μl) was added to each homogenized brain. On the other hand, ethanol from which the compound (I) was removed was added to a control group of homogenized brain. A malonodialdehyde was measured by the (TBA) method disclosed in Okawa et al., Analysis Biochemistry, Vol. 95, page 351 (1979). The produced lipoperoxide was calculated based on the measured value of malonodialdehyde.

Table 2 shows inhibition rates (%) of the production of the lipoperoxide wherein $10^{-5}$M of test compounds were added and 50% inhibitory concentration (IC$_{50}$, M).

TABLE 2

| Test Compound (Example No.) | Lipoperoxide Inhibitory Activity | |
|---|---|---|
| | ACAT Inhibition Rate (%, $10^{-5}M$) | IC$_{50}$ (M) |
| 12 | 98.5 | |
| 13 | 71.6 | |
| 14 | 98.4 | $3.7 \times 10^{-7}$ |
| 15 | 98.2 | $8.9 \times 10^{-7}$ |
| 16 | 100 | $1.2 \times 10^{-6}$ |
| 27 | 90.2 | |
| 32 | 99.7 | $4.0 \times 10^{-7}$ |
| 33 | 96.1 | $1.3 \times 10^{-6}$ |
| 34 | 62.1 | |
| 35 | 84.9 | $8.1 \times 10^{-7}$ |
| 38 | 98.2 | |

EXAMPLE 1

To a mixture of 3-amino-4-(2-chlorophenyl)-6,8-dimethylquinoline (1.02 g), 3,5-di-tert-butyl-4-hydroxy benzoic acid (750 mg), diethylphosphoryl cyanide (DEPC) (587 mg) and N,N-dimethylformamide (100 mg) was dropwise added a solution of triethylamine (0.51 ml) in DMF (2 ml) under stirring at 0° C. The mixture was stirred at 0° C. for 30 minutes and at room temperature for one night. Then, the mixture was diluted with water and extracted with ethyl acetate. The ethyl acetate layer was concentrated after being washed with water and dried (MgSO$_4$). The residue was purified by a silica gel column chromatography with hexane-ethyl acetate (85:15,V/V), and then crystallized from methanol to give 4-(2-chlorophenyl)-3-(3,5-di-tert-butyl-4-hydroxybenzamido)-6,8-dimethylquinoline (373 mg, 24.2%). Recrystallization from methanol gave colorless prisms of mp 127°-129° C.

Elemental analysis for C$_{32}$H$_{35}$ClN$_2$O$_2$ Calculated: C 74.62; H 6.85; N 5.44 Found : C 74.53; H 6.96; N 5.24

EXAMPLE 2

By the same method as in Example 1, 6-chloro-3-(3,5-di-tert-butyl-4-hydroxybenzamido)-4-phenylquinoline was obtained.

Yield: 23.0% mp: 232°-235° C. (recrystallized from acetone-isopropyl ether)

Elemental analysis for C$_{30}$H$_{31}$ClN$_2$O$_2$ Calculated: C 73.98; H 6.42; N 5.75 Found : C 74.12; H 6.67; N 5.43

EXAMPLE 3

By the same method as in Example 1, 3-(3,5-di-tert-butyl-4-hydroxybenzamido)-6-chloro-4-(3,4-dimethoxyphenyl)quinoline was obtained.

Yield: 15.7% mp: 293°-294° C. (from ethyl acetate-hexane)

Elemental analysis for C$_{32}$H$_{35}$ClN$_2$O$_4$ Calculated: C 70.25; H 6.45; N 5.12 Found : C 70.34; H 6.52; N 4.87

EXAMPLE 4

To a solution of 3,5-di-tert-butyl-4-hydroxybenzoic acid (220 mg) in dichloromethane (20 ml) was dropwise added dicyclohexylcarbodiimide (DCC) (180 mg) under stirring at 0° C. The mixture was stirred at 0° C. for 15 minutes. Then, 3-amino-6-chloro-4-(2,3,4-trimethoxyphenyl) quinoline (250 mg) was added to this mixture. The resultant mixture was stirred at 0° C. for an hour and at room temperature for two days. After the residue was filtered off, the filtrate was diluted with water and extracted with dichloromethane. The dichloromethane layer was washed with an aqueous sodium hydroxide solution, diluted with hydrochloric acid and water in this order and dried (MgSO$_4$). The solvent was removed and the residue was purified by a silica gel column chromatography with hexane-ethyl acetate (3:1, V/V), and then crystallized from isopropyl ether to obtain 3-(3,5-di-tert-butyl-4-hydroxybenzamido)-6-chloro-4-(2,3,-4-trimethoxyphenyl) quinoline (199 mg, 47.6%).

mp: 190°–192° C.

Elemental analysis for $C_{33}H_{37}ClN_2O_5$ Calculated: C 68.68; H 6.46; N 4.85 Found : C 68.97; H 6.50; N 4.77

EXAMPLE 5

To a solution of 3-amino-4-(2-chlorophenyl)-6,8-dimethylquinoline (565 mg) in dichloromethane (20 ml) was dropwise added 3,4,5-drimethoxybenzoyl chloride (690 mg) under stirring. The mixture was stirred for two days and poured into ice-water. Then, the resultant solution was made alkaline with an aqueous sodium hydroxide solution and extracted with dichloromethane. The dichloromethane layer was washed with water and dried (MgSO$_4$). The solvent was removed and the residue was recrystallized from isopropyl ether to obtain 4-(2-chlorophenyl)-3-(3,4,5-trimethoxybenzamido)-6,8-dimethylquinoline (860 mg, 90.2%) as colorless needles.

mp: 187°–190° C.

Elemental analysis for $C_{27}H_{25}ClN_2O_4$ Calculated: C 67.99; H 5.28; N 5.87 Found : C 67.77; H 5.29; N 5.78

EXAMPLE 6

A mixture of 4-acetoxy-3,5-diisopropylbenzoic acid (634 mg), thionyl chloride (3 ml) and DMF (1 drop) was refluxed for 40 minutes, concentrated and evaporated to obtain 4-acetoxy-3,5-diisopropylbenzoyl chloride. The resultant was dissolved in dichloromethane (20 ml), to which 3-amino-4-(2-chlorophenyl)-6,8-dimethylquinoline (566 mg) and triethylamine (0.30 ml) were added. Thus obtained solution was stirred at room temperature for one night. After dilution with water, the solution was extracted with dichloromethane. The dichloromethane layer was washed with 2N-hydrochloric acid and water, and then dried (MgSO$_4$). The solvent was removed and the residue was recrystallized from ethanol to obtain 3-(4-acetoxy-3,5-diisopropylbenzamido)-4-(2-chlorophenyl)-6,8-dimethylquinoline (815 mg, 77.0%) as colorless prisms.

mp: 195°–196° C.

Elemental analysis for $C_{32}H_{33}ClN_2O_3$ Calculated: C 72.65; H 6.29; N 5.29 Found : C 72.67; H 6.32; N 5.21

EXAMPLE 7

A mixture of 3-(4-acetoxy-3,5-diisopropylbenzamido)-4-(2-chlorophenyl)-6,8-dimethylquinoline (600 mg), methanol (40 ml) and 1N-sodium hydroxide (4 ml) was stirred at room temperature for 3 hours. After concentrating, the mixture was diluted with water and made acidic with 2N-hydrochloric acid. Thereafter, the mixture was extracted with ethyl acetate. The ethyl acetate layer was washed with water and dried (MgSO$_4$). The solvent was removed and the residue was recrystallized from acetone-isopropyl ether to give 4-(2-chlorophenyl)-3-(4-hydroxy-3,5-diisopropyl benzamido)-6,8-dimethylquinoline (494 mg, 89.5%) as colorless prisms.

mp: 237–238° C.

Elemental analysis for $C_{30}H_{31}ClN_2O_2$ Calculated: C 73.98; H 6.42; N 5.75 Found : C 73.86; H 6.55; N 5.64

EXAMPLE 8

By the same method as in Example 6, 3-(4-acetoxy-3,5-dimethylbenzamido)-4-(2-chlorophenyl)-6,8-dimethylquinoline methanol solvate was obtained as colorless prisms.

Yield: 86.3% mp: 134°–136° C. (from methanol)

Elemental analysis for $C_{28}H_{25}ClN_2O_3 \cdot CH_4O$ Calculated: C 68.97; H 5.79; N 5.54 Found : C 69.28; H 5.62; N 5.51

EXAMPLE 9

By the same method as in Example 6, 3-(4-acetoxy-2,3,5-trimethylbenzamido)-4-(2-chlorophenyl)-6,8-dimethylquinoline was obtained as colorless prisms.

Yield: 89.4% mp: 180°–182° C. (from ethyl ether-isopropyl ether)

Elemental analysis for $C_{29}H_{27}ClN_2O_3$ Calculated: C 71.52; H 5.59; N 5.75 Found : C 71.19; H 5.56; N 5.75

EXAMPLE 10

By the same method as in Example 7, 3-( 2-chlorophenyl )-3-( 4-hydroxy-3,5-dimethylbenzamido)-6,8-dimethylquinoline was obtained as colorless prisms.

Yield: 85.0% mp: 193°–194° C. (from isopropyl ether - acetic acid)

Elemental analysis for $C_{26}H_{23}ClN_2O_2$ Calculated: C 72.47; H 5.38; N 6.50 Found : C 72.38; H 5.35; N 6.47

EXAMPLE 11

By the same method as in Example 7, 4-(2-chlorophenyl)-3-(4-hydroxy-2,3,5-trimethylbenzamido)-6,8-dimethylquinoline was obtained as colorless prisms.

Yield: 82.8% mp: 261°–264° C. (from acetone)

Elemental analysis for $C_{27}H_{25}ClN_2O_2$ Calculated: C 72.88; H 5.66; N 6.30 Found : C 72.95; H 5.66; N 6.38

EXAMPLE 12

To a solution of 6-hydroxy-2,5,7,8-tetramethylchroman-2-carboxylic acid (1.34 g) in dichloromethane (100 ml) was dropwise added DCC (945 mg) under stirring at a temperature of 0° C. The mixture was stirred at 0° C. for 15 minutes, and 3-amino-4-(2-chlorophenyl)-6,8-dimethylquinoline (1.04 g) was added thereto. Thus resulting mixture was further stirred at 0° C. for an hour and at room temperature for one night. The reaction mixture was filtered and the filtrate was concentrated. The residue was purified by a silica gel column chromatography with hexane-ethyl acetate (8:2,V/V), and then crystallized from acetone to give 4-(2-chlorophenyl)-3-(6-hydroxy-2,5,7,8-tetramethylchroman-2-ylcarbonyl)amino-6,8-dimethylquinoline (341 mg, 18.0%) as colorless prisms.

mp: 222°–224° C.

Elemental analysis for $C_{31}H_{31}ClN_2O_3$ Calculated: C 72.29; H 6.07; N 5.44 Found : C 72.25; H 6.10; N 5.42

EXAMPLE 13

By the same method as in Example 12, 5-acetoxy-2,3-dihydro-2,4,7,8-tetramethylbenzofuran-2-carboxylic acid was reacted with DCC and 3-amino-4-(2-chlorophenyl)-6,8-dimethylquinoline in this order to give 3-(5-acetoxy-2,3-dihydro-2,4,6,7-tetramethylbenzofuran-2-ylcarbonyl)amino-4-(2-chlorophenyl) -6,8-dimethylquinoline as colorless prisms.

Yield: 38.3% mp: 259°–261° C.

Elemental analysis for $C_{32}H_{31}ClN_2O_4$ Calculated: C 70.77; H 5.75; N 5.16 Found : C 70.48; H 5.92; N 5.05

EXAMPLE 14

A mixture of 3-(5-acetoxy-2,3-dihydro-2,4,6,7-tetramethylbenzofuran-2-ylcarbonyl)amino-4-(2-chlorophenyl) -6,8-dimethylquinoline (400 ml) and 6.92N-hydrochloric acid-methanol solution (10 ml) was stirred at room temperature for eight hours. After addition of water, the mixture was extracted with ethyl acetate. The ethyl acetate layer was washed with water and dried (MgSO$_4$), then concentrated. The residue was purified by a silica gel column chromatography with hexane-ethyl acetate (3:1,V/V), and then crystallized from isopropyl ether to give 4-(2-chlorophenyl)-3-(2,3-dihydro-5-hydroxy-2,4,6,7-tetramethylbenzofuran-2-ylcarbonyl) amino-6,8-dimethylquinoline (104 mg, 28.2%) as colorless prisms.

mp: 204°–206° C.

Elemental analysis for C$_{30}$H$_{29}$ClN$_2$O$_3$ Calculated: C 71.92; H 5.83; N 5.59 Found : C 72.23; H 5.86; N 5.65

EXAMPLE 15

A mixture of 3-amino-4-(2-chlorophenyl)-6,8dimethylquinoline (1.0 g), triethylamine (2 drops) and benzene (5 ml) was heated to 70° C., and diketene (0.25 ml) was dropwise added thereto. The mixture was further heated at 70° C. for 30 minutes, and then, dimethylsulfoxide (15 ml) and 2-aminothiophenol (0.4 g) were added thereto. The resultant mixture was heated at 130° C. for an hour, diluted with water and extracted with ethyl acetate. The ethyl acetae layer was washed with a solution of salt and dried (MgSO$_4$). The solvent was removed and the residue was purified by a silica gel column chromatography with hexane-ethyl acetate (3:l,V/V), and then crystallized from ethyl acetate-ethyl ether to give 4-(2-chlorophenyl)-6,8-dimethyl-3-(3-methyl-4H-1,4-benzothiazin-2-carbonyl) aminoquinoline (0.39 g, 26%) as yellowish prisms.

mp: 177°–178° C.

Elemental analysis for C$_{27}$H$_{22}$ClN$_3$OS Calculated: C 68.71; H 4.70; N 8.90 Found : C 68.69; H 4.63; N 8.72

EXAMPLE 16

By the same method as in Example 15, 4-(2-chlorophenyl)-3-(7-fluoro-3-methyl-4H-1,4-benzothiazin-2-ylcarbonyl) amino-6,8-dimethylquinoline was obtained as yellowish prisms.

Yield: 26.0% mp: 182°–183° C. (from ethyl acetate-ethyl ether)

Elemental analysis for C$_{27}$H$_{21}$ClFN$_3$OS Calculated: C 66.18; H 4.32; N 8.58 Found : C 66.19; H 4.35; N 8.69

EXAMPLE 17

To a mixture of 3-amino-4-(2-chlorophenyl)-6,8-dimethylquinoline (564 mg), potassium carbonate (280 mg), ethyl acetate (8 ml) and water (4 ml) was dropwise added 2,4-dimethylphenylacetyl chloride (400 mg) in ethyl acetate (2 ml) under ice-cooling and stirring. Then, the mixture was heated to room temperature and stirred for 30 minutes. Thereafter, the organic layer was taken out, washed with water and dried (MgSO$_4$). The solvent was removed, and the residue was recrystallized from isopropyl ether to give crystals (541 mg, 60.1%). The crystals were recrystallized from ethanol to obtain 4-(2-chlorophenyl)-6,8-dimethyl-3-(2,4-dimethylphenyl acetylamino)quinoline as colorless prisms.

mp: 132°–133° C.

Elemental analysis for C$_{27}$H$_{25}$ClN$_2$O Calculated: C 75.60; H 5.87; N 6.53 Found : C 75.60; H 5.88; N 6.48

EXAMPLE 18

By the same method as in Example 17, 4-(2-chlorophenyl)-3-(2,4-difluorophenylacetylamino)-6,8-dimethylquinoline was obtained as colorless prisms.

Yield: 79.3% mp: 133°–134° C. (from ethanol)

Elemental analysis for C$_{25}$H$_{19}$ClF2N$_2$O Calculated: C 68.73; H 4.39; N 6.41 Found : C 68.88; H 4.44; N 6.45

EXAMPLE 19

By the same method as in Example 17, 4-(2-chlorophenyl)-3-(2,4-diisopropylphenylacetylamino)-6,8-dimethylquinoline was obtained as colorless prisms.

Yield: 73.2% mp: 127°–128° C. (from ethanol)

Elemental analysis for C$_{31}$H$_{33}$ClN$_2$O Calculated: C 76.76; H 6.86; N 5.78 Found : C 77.04; H 6.87; N 5.78

EXAMPLE 20

To a solution of 3-amino-4-(2-chlorophenyl)-6,8-dimethylquinoline (282 mg) and triethylamine (0.14 ml) in dichloromethane (4 ml) was dropwise added 3,5-di-tert-butyl-4-hydroxyphenylacetyl chloride (340 mg) under ice-cooling. The solution was stirred under ice-cooling for an hour, washed with water and dried (MgSO$_4$). The solvent was removed, and the residue was recrystallized from isopropyl ether-hexane to give crystals (362 mg, 68.4%). The crystals were recrystallized from ethanol to obtain 3-(3,5-di-tert-butyl-4-hydroxyphenylacetylamino)-4-(2-chlorophenyl)-6,8-dimethylquinoline as colorless prisms.

mp: 189°–190° C.

Elemental analysis for C$_{33}$H$_{37}$ClN$_2$O$_2$ Calculated: C 74.91; H 7.05; N 5.29 Found : C 74.86; H 6.84; N 5.36

EXAMPLE 21

To a solution of 3-amino-4-(2-chlorophenyl)-6,8-dimethylquinoline (3.38 g) in tetrahydrofuran (30 ml) was added 3,4-diacetoxycinnamoyl chloride (3,38 g). After being stirred at room temperature for 15 hours, the solution was diluted with water and extracted with ethyl acetate. The ethyl acetate layer was washed with water and dried (MgSO$_4$). The solvent was removed, and the residue was crystallized from isopropyl ether to give crystals (5.2 g, 98.5%). The crystals were recrystallized from acetone-hexane to obtain 3-(3,4-diacetoxycinnamoylamino)-4-(2-chlorophenyl)-6,8-dimethylquinoline as colorless needles.

mp: 196°–197° C.

Elemental analysis for C$_{30}$H$_{25}$ClN$_2$O$_5$ Calculated: C 68.12; H 4.76; N 5.30 Found : C 68.12; H 4.73; N 5.21

EXAMPLE 22

By the same method as in Example 21, 4-(2-chlorophenyl)-3-(3,4-dimethoxycinnamoylamino)-6,7-dimethylquinoline was obtained as colorless prisms.

Yield: 83.0% mp: 210°–211° C. (from ethanol)

Elemental analysis for C$_{28}$H$_{25}$ClN$_2$O$_3$ Calculated: C 71.11; H 5.33; N 5.92 Found : C 71.16; H 5.39; N 5.84

EXAMPLE 23

By the same method as in Example 21, 4-(2-chlorophenyl)-3-(4-methoxycarbonylcinnamoylamino)-6,8-dimethylquinoline was obtained as colorless prisms.

Yield: 45.7% mp: 225°–226° C. (from acetone)

Elemental analysis for $C_{28}H_{23}ClN_2O_3$ Calculated: C 71.41; H 4.92; N 5.95 Found : C 71.20; H 4.95; N 5.87

EXAMPLE 24

By the same method as in Example 21, 4-(2-chlorophenyl)-3-(2,3-dimethoxycinnamoylamino)-6,8-dimethylquinoline ½ hydrate was obtained as colorless prisms.
Yield: 74.6%
mp: 154°–155° C. (from ethanol)
Elemental analysis for $C_{28}H_{25}ClN_2O_3 \cdot \tfrac{1}{2}H_2O$ Calculated: C 69.78; H 5.44; N 5.88 Found : C 70.00; H 5.43; N 5.88

EXAMPLE 25

By the same method as in Example 21, 4-(2-chlorophenyl)-3-(2,5-dimethoxycinnamoylamino)-6,8-dimethylquinoline was obtained as colorless needles.
Yield: 86.0%
mp: 209°–210° C. (from acetone) Elemental analysis for $C_{28}H_{25}ClN_2O_3$ Calculated: C 71.11; H 5.33; N 5.92 Found : C 71.50; H 5.37; N 5.95

EXAMPLE 26

By the same method as in Example 21, 3-(4-acetoxy-3-methoxycinnamoylamino)-4-(2-chlorophenyl)-6,8-dimethylquinoline was obtained as colorless prisms.
Yield: 74.0%
mp: 174°–175° C. (from ethanol)
Elemental analysis for $C_{29}H_{25}ClN_2O_4$ Calculated: C 69.53; H 5.03; N 5.59 Found : C 69.17; H 5.12; N 5.26

EXAMPLE 27

By the same method as in Example 21, 3-(4-acetoxy-3,5-dimethoxylcinnamoylamino)-4-(2-chlorophenyl)-6,8-dimethylquinoline was obtained as colorless prisms.
Yield: 83.8%
mp: 152°–154° C. (from ethanol)
Elemental analysis for $C_{30}H_{27}ClN_2O_5$ Calculated: C 67.86; H 5.13; N 5.28 Found : C 67.53; H 5.07; N 5.26

EXAMPLE 28

By the same method as in Example 21, 3-(4-acetoxy-3,5-dimethylcinnamoylamino)-4-(2-chlorophenyl)-6,8-dimethylquinoline was obtained as colorless needles.
Yield: 94.2%
mp: 207°–208° C. (from ethanol)
Elemental analysis for $C_{30}H_{27}ClN_2O_3$ Calculated: C 72.21; H 5.45; N 5.61 Found : C 72.28; H 5.48; N 5.41

EXAMPLE 29

By the same method as in Example 21, 3-(4-acetoxy-2,3,5-trimethylcinnamoylamino)-4-(2-chlorophenyl)-6,8-dimethylquinoline was obtained as colorless needles.
Yield: 94.8%
mp: 233°–234° C. (from ethanol-chloroform)
Elemental analysis for $C_{31}H_{29}ClN_2O_3$ Calculated: C 72.58; H 5.70; N 5.46 Found : C 72.44; H 5.68; N 5.47

EXAMPLE 30

1-Hydroxybenzotriazole (154 mg) and dicyclohexylcarbodiimide (272 mg) were added to a solution of 3,5-di-tert-butyl-4-hydroxycinnamic acid (331 mg) in DMF (5 ml). The mixture was stirred at room temperature for 5 minutes, and then, 3-amino-4-(2-chlorophenyl)-6,8-dimethylquinoline (288 mg) was added thereto. The resultant mixture was further stirred at room temperature for 24 hours. The insoluble materials were filtered off, while the filtrate was diluted with water and extracted with ethyl acetate. The ethyl acetate layer was washed with water and dried ($MgSO_4$). The solvent was removed, and the residue was purified by a silica gel chromatography with benzene-acetone (9:1), then, crystallized from isopropyl ether to give 3-(3,5-di-tert-butyl-4-hydroxycinnamoylamino)-4-(2-chlorophenyl)-6,8-dimethylquinoline (257 mg, 47.5%) as colorless needles.
mp: 227°–228° C.
Elemental analysis for $C_{34}H_{37}ClN_2O_2$ Calculated: C 75.43; H 6.89; N 5.18 Found : C 75.28; H 7.00; N 5.18

EXAMPLE 31

A solution of boron tribromide in dichloromethane (1:2, 1 ml) was added to a solution of 4-(2-chlorophenyl)-3-(3,4-dimethoxycinnamoylamino)-6,8-dimethylquinoline (473 mg) in dichloromethane (5 ml) under ice-cooling. After being stirred for 20 minutes under ice-cooling, and further for 30 minutes at room temperature, the mixture was poured into ice water. The solution was made neutral with a sodium hydrogen carbonate saturated solution and was extracted with ethyl acetate. The ethyl acetate layer was washed with water and dried ($MgSO_4$). The solvent was removed, and the residue was crystallized to give crystals of 4-(2-chlorophenyl)-3-(3,4-dihydroxycinnamoylamino)-6,7-dimethylquinoline (212 mg, 44.8%). The crystals were recrystallized from acetone to obtain yellowish prisms (⅔ acetone solvate).
mp: 272°–274° C.
Elemental analysis for $C_{26}H_{21}ClN_2O_3 \cdot \tfrac{1}{2}C_3H_6O$ Calculated: C 69.69; H 5.10; N 5.91 Found : C 69.44; H 4.86; N 6.06

EXAMPLE 32

A solution of boron tribromide in dichloromethane (1:2, 2 ml) was dropwise added to a solution of 4-(2-chlorophenyl)-3-(2,3-dimethoxycinnamoylamino)-6,8-dimethylquinoline (0.94 g) in dichloromethane (15 ml) under ice-cooling and stirring. After being stirred for 30 minutes under ice-cooling, and further for 1.5 hours at room temperature, the mixture was poured into ice water. The solution was made neutral with a sodium hydrogen carbonate saturated solution and was extracted with ethyl acetate. The ethyl acetate layer was washed with water and dried ($MgSO_4$). The solvent was removed, and the residue was dissolved into ethyl acetate (5 ml), to which 4N HCl-ethyl acetate solution (2 ml) was added to give crystals of 4-(2-chlorophenyl)-3-(2,3-dihydroxycinnamoylamino)-6,8-dimethylquinoline hydrochloric acid salt hydrate (0.85 g, 83.3%). The crystals were recrystallized from ethanol to obtain yellowish needles.
mp: 253°–256° C.
Elemental analysis for $C_{26}H_{21}ClN_2O_3 \cdot HCl \cdot 3/2H_2O$ Calculated: C 61.43; H 4.96; N 5.51 Found : C 61.73; H 5.01; N 5.44

EXAMPLE 33

A mixture of 3-(4-acetoxy-3,5-dimethoxycinnamoylamino)-4-(2-chlorophenyl)-6,8-dimethylquinoline (300 mg), 2N sodium hydroxide (1.2 ml), methanol (3 ml) and dioxane (3 ml) was heated at 60° C.–70° C. for 10 minutes and then diluted with water. After being adjusted to pH 4 by addition of 2N hydrochloric acid, the mixture was extracted with chloroform. The chloroform layer was washed with water and dried (MgSO₄). The solvent was removed, and the residue was crystallized from ether to give crystals of 4-(2-chlorophenyl)-3-(4-hydroxy-3,5-dimethoxycinnamonylamino)-6,8-dimethylquinoline (230 mg, 76.2%). The crystals were recrystallized from ethanol to afford colorless prisms.

mp: 140°–143° C.

Elemental analysis for $C_{28}H_{25}ClN_2O_4$ Calculated: C 67.36; H 5.84; N 5.24 Found : C 67.37; H 5.87; N 5.27

EXAMPLE 34

By the same method as in Example 33, 4-(2-chlorophenyl)-3-(4-hydroxy-3,5-dimethylcinnamoylamino)-6,8-dimethylquinoline was obtained as pale yellowish prisms.

Yield: 69.7% mp: 249°–251° C. (from acetone-hexane)

Elemental analysis for $C_{28}H_{25}ClN_2O_2$ Calculated: C 73.56; H 5.51; N 6.13 Found : C 73.83; H 5.57; N 6.16

EXAMPLE 35

By the same method as in Example 33, 4-(2-chlorophenyl)-3-(4-hydroxy-2,3,5-trimethylcinnamoylamino)-6,8-dimethylquinoline hydrate was obtained as colorless prisms.

Yield: 80.5% mp: 160°–163° C. (from acetone)

Elemental analysis for $C_{29}H_{27}ClN_2O_2 \cdot H_2O$ Calculated: C 71.23; H 5.98; N 5.73 Found : C 71.54; H 6.08; N 5.79

EXAMPLE 36

A mixture of 3,4-dimethoxycinnamoyl chloride (678 mg), 3-amino-4-(2-chlorophenyl)-1,6,8-trimethyl-2(1H)quinolone (511 mg), pyridine (0.28 ml) and THF (10 ml) was stirred at room temperature for four days. Then, the mixture was diluted with water and extracted with ethyl acetate. The ethyl acetate layer was washed with water and dried (MgSO₄). The solvent was removed and the residue was purified by a silica gel chromatography with benzene-acetone (4:1) to give crystals of 4-(2-chlorophenyl)-3-(3,4-dimethoxycinnamoylamino)-1,6,8-trimethyl-2(1H)-quinolone hydrate (510 mg, 65.6%). The crystals were recrystallized from ethanol to afford colorless prisms.

Elemental analysis for $C_{29}H_{27}ClN_2O_4 \cdot H_2O$ Calculated: C 66.85; H 5.61; N 5.38 Found : C 67.01; H 5.27; N 5.36

EXAMPLE 37

By the same method as in Example 33, 4-(2-chlorophenyl)-3-(4-hydroxy-3-methoxycinnamoylamino)-6,8-dimethylquinoline ethanol solvate was obtained as colorless prisms.

Yield: 68.7% mp: 133°–134° C. (from ethanol-chloroform)

Elemental analysis for $C_{27}H_{23}ClN_2O_3 \cdot C_2H_5OH$ Calculated: C 68.97; H 5.79; N 5.55 Found : C 69.26; H 5.88; N 5.60

EXAMPLE 38

A mixture of 3-(3,4-diacetoxycinnamoylamino)-4-(2chlorophenyl)-6,8-dimethylquinoline (4.0 g), potassium carbonate (3.13 g) and dioxane-methanol-water (2:2:1, 50 ml) was stirred at room temperature for 3 hours in a stream of argon gas, then diluted with water. After being adjusted to pH 4 by addition of 2N hydrochloric acid, the mixture was extracted with ethyl acetate. The ethyl acetate layer was washed with water and dried (MgSO₄). The solvent was removed, and the residue was crystallized from isopropyl ether to give crystals of 4-(2-chlorophenyl)-3-(3,4-dihydroxycinnamoylamino)-6,8-dimethylquinoline (2.7 g, 80.4%). The crystals were recrystallized from ethyl acetate to afford pale yellowish prisms.

mp: 224°–226° C.

Elemental analysis for $C_{26}H_{19}ClN_2O_3$ Calculated: C 70.19; H 4.76; N 6.30 Found : C 70.12; H 4.77; N 6.28

EXAMPLE 39

A mixture of 3-amino-4-(2-chlorophenyl)-6,8-dimethylquinoline (282 mg), 4-acetoxycinnamoyl chloride (250 mg) and tetrahydrofuran (5 ml) was stirred at room temperature for 6 hours. After being diluted with water and made neutral with a sodium hydrogen carbonate saturated solution, the mixture was extracted with ethyl acetate. The ethyl acetate layer was washed with water and dried (MgSO₄). The solvent was removed, and the residue was dissolved in tetrahydrofuran-methanol solution (1:1, 6 ml). Then, 2N-hydrochloric acid was added to the solution which was thereafter stirred at room temperature for 1.5 hours. The resultant solution was diluted with water, adjusted to pH 4 by addition of 2N-hydrochloric acid and extracted with ethyl acetate. The ethyl acetate layer was washed with water and dried (MgSO₄). The resultant was removed to give crystals of 4-(2-chlorophenyl)-3-(4-hydroxycinnamoylamino)-6,8-dimethylquinoline (335 mg, 78.3%). The obtained crystals were recrystallized from ethanol to afford colorless needles.

mp: 228°–230° C.

Elemental analysis for $C_{28}H_{21}ClN_2O_2$ Calculated: C 72.81; H 4.93; N 6.53 Found : C 72.81; H 4.90; N 6.47

EXAMPLE 40

5% of palladium-carbon (including 50% water, 40 mg) was added to a solution of 3-(4-acetoxy-3,5-dimethylcinnamoylamino)-4-(2-chlorophenyl)-6,8-dimethylquinoline (200 mg) in tetrahydrofuran-methanol (1:1, 5 ml). The solution was catalytically reduced at room temperature under atmospheric pressure. After the reduction, the catalyst was removed and the filtrate was concentrated to give crystals of 3-[3-(4-acetoxy-3,5-dimethylphenyl) propionylamino]-4-(2-chlorophenyl)-6,8-dimethylquinoline. The crystals were recrystallized from ethanol to afford colorless needles (146 mg, 73.0%)

mp: 178°–179° C.

Elemental analysis for $C_{30}H_{29}ClN_2O_3$ Calculated: C 71.92; H 5.83; N 5.59 Found : C 71.79; H 5.86; N 5.57

EXAMPLE 41

By the same method as in Example 40, 4-(2-chlorophenyl)-3-[3-(2,3-dihydroxyphenyl)propionylamino]-6,8-dimethylquinoline was obtained as colorless prisms.

Yield: 77.1% mp: 181°–182° C. (from ethanol-isopropylether)

Elemental analysis for $C_{26}H_{23}ClN_2O_3$ Calculated: C 69.87; H 5.19; N 6.27 Found : C 69.43; H 5.19; N 6.19

EXAMPLE 42

A mixture of 3,4-dimethoxycinnamic acid (0.94 g) and thionyl chloride (3 ml) was refluxed for 20 minutes under heating, and then, the surplus thionyl chloride was removed. Thereafter, the residue was dissolved in tetrahydrofuran (15 ml), to which 3-amino-6-chloro-4(2-chlorophenyl)-quinoline (0.87 g) and pyridine (0.5 ml) were added. The resultant mixture was stirred for 5 hours at room temperature, followed by diluting with water and extracting with ethyl acetate. The ethyl acetate layer was washed with water and dried (MgSO$_4$). The solvent was removed, and the residue was crystallized from chloroform-ethanol to give 6-chloro-4-(2-chlorophenyl)-3(3,4-dimethoxycinnamoylamino)quinoline as colorless plate crystals.

mp: 208°–209° C.

Elemental analysis for $C_{26}H_{20}Cl_2N_2O_3$ Calculated: C 65.15; H 4.21; N 5.84 Found : C 64.98; H 4.13; N 5.79

EXAMPLE 43

By the same method as in Example 38, 6-chloro-4-(2-chlorophenyl)-3-(3,4-dihydroxycinnamoylamino)-quinoline hydrobromide was obtained as yellowish crystals.

Yield: 64.9% mp: 260°–264° C. (decomposition, recrystallized from ethanol)

Elemental analysis for $C_{24}H_{26}Cl_2N_2O_3 \cdot HBr$ Calculated: C 54.16; H 3.22; N 5.26 Found : C 54.18; H 3.49; N 5.05

EXAMPLE 44

By the same method as in Example 21, 4-(2-chlorophenyl)-3-(3,4-dimethoxycinnamoylamino)-6,8-dimethylquinoline ethanol solvate was obtained as colorless prisms.

Yield: 71.8% mp: 115°–116° C. (from ethanol)

Elemental analysis for $C_{28}H_{25}ClN_2O_3 \cdot C_2H_5OH$ Calculated: C 69.42; H 6.02; N 5.40 Found : C 69.26; H 5.99; N 5.35

EXAMPLE 45

By the same method as in Example 21, 4-(2-chlorophenyl)-6,8-dimethyl-3-(3,4,5-trimethoxycinnamoylamino) quinoline was obtained as colorless needles.

Yield: 83.9% mp: 198°–200° C. (from ethanol)

Elemental analysis for $C_{29}H_{27}ClN_2O_4$ Calculated: C 69.25; H 5.41; N 5.57 Found : C 69.29; H 5.46; N 5.49

EXAMPLE 46

By the same method as in Example 21, 4-(2-chlorophenyl)-6,8-dimethyl-3-(2,3,4-trimethoxycinnamoylamino) quinoline was obtained as colorless needles.

Yield: 80.7% mp: 200°–201° C. (from ethanol)

Elemental analysis for $C_{29}H_{27}ClN_2O_4$ Calculated: C 69.25; H 5.41; N 5.57 Found : C 69.48; H 5.40; N 5.64

EXAMPLE 47

By the same method as in Example 21, 3-(4-acetoxy-3,5-dimethoxycinnamoylamino)-4-phenyiquinoline was obtained as pale yellowish prisms.

Yield: 92.1% mp: 247°–248° C. (from chloroform-ethanol)

Elemental analysis for $C_{28}H_{24}N_2O_5$ Calculated: C 71.78; H 5.16; N 5.98 Found : C 71.68; H 5.24; N 5.65

EXAMPLE 48

By the same method as in Example 21, 3-(4-acetoxy-3,5-dimethoxycinnamoylamino)-4-(2-chlorophenyl)-quinoline was obtained as colorless prisms.

Yield: 58.4% mp: 237°–238° C. (from ethanol)

Elemental analysis for $C_{28}H_{23}ClN_2O_5$ Calculated: C 66.87; H 4.61; N 5.57 Found : C 66.50; H 4.72; N 5.45

EXAMPLE 49

By the same method as in Example 21, 3-(4-acetoxy-3,5-dimethoxycinnamoylamino)-4-(2-chlorophenyl)-6-isopropylquinoline was obtained as colorless needles.

Yield: 76.1% mp: 138°–138° C. (from ethanol-hexane)

Elemental analysis for $C_{31}H_{29}ClN_2O_5$ Calculated: C 68.32; H 5.36; N 5.14 Found : C 68.10; H 5.78; N 4.68

EXAMPLE 50

By the same method as in Example 36, 3-(4-acetoxy-3,5-dimethoxycinnamoylamino)-4-(2-chlorophenyl)-6-isopropyl-1-methyl-2(1H)-quinolone was obtained as colorless prisms.

Yield: 57.0% mp: 187°–189° C. (from ethanol)

Elemental analysis for $C_{32}H_{31}ClN_2O_6$ Calculated: C 66.84; H 5.43; N 4.87 Found : C 66.49; H 5.31; N 4.81

EXAMPLE 51

By the same method as in Example 36, 3-(4-acetoxy-3,5-dimethoxycinnamoylamino)-4-(2-chlorophenyl)-1,6,7-trimethyl-2(1H)-quinolone was obtained as colorless needles.

Yield: 84.3% mp: 259°–260° C. (from acetone)

Elemental analysis for $C_{31}H_{29}ClN_2O_6$ Calculated: C 66.37; H 5.21; N 4.99 Found : C 66.46; H 5.20; N 4.85

EXAMPLE 52

The 3-(4-acetoxy-3,5-dimethoxycinnamoylamino)-6-nitro-4-phenylquinoline (0.95 g) obtained in Example 21 was dissolved in dioxane-methanol (1:1, 20 ml), to which 2NNaOH (3 ml) was added. The resultant solution was stirred for 30 minutes at room temperature, and then, adjusted to pH 4 by addition of 2N HCl, resulting in obtaining crystals of 3-(4-hydroxy-3,5-dimethoxycinnamoylamino)-6-nitro-4-phenylquinoline. The crystals were recrystallized from acetone to give yellowish needles (0.363 g, 38.5%).

mp: 198°–199° C.

Elemental analysis for $C_{26}H_{21}N_3O_6$ Calculated: C 66.24; H 4.49; N 8.91 Found : C 66.26; H 4.64; N 8.61

EXAMPLE 53

By the same method as in Example 21, 3-(4-acetoxy-3,5-dimethoxycinnamoylamino)-4-(2-chlorophenyl)-6-methylquinoline ¼ acetone solvate was obtained as colorless prisms.

Yield: 44.5% mp: 236°–237° C. (from acetone)

Elemental analysis for $C_{29}H_{25}ClN_2O_5 \cdot \frac{1}{4}(CH_3)_2CO$ Calculated: C 67.23; H 5.03; N 5.27 Found : C 67.10; H 4.95; N 5.19

EXAMPLE 54

By the same method as in Example 21, 3-(4-acetoxy-3,5-dimethoxycinnamoylamino)-4-(2-chlorophenyl)-6-ethylquinoline was obtained as colorless needles.
Yield: 71.3%
mp: 136°–137° C. (from acetone-isopropyl ether)
Elemental analysis for $C_{30}H_{27}ClN_2O_5$ Calculated: C 67.86; H 5.13; N 5.28 Found : C 67.63; H 5.13; N 5.25

EXAMPLE 55

By the same method as in Example 21, 3-(4-acetoxy-3,5-dimethoxycinnamoylamino)-4-(2-chlorophenyl)-6,7-dimethylquinoline ½ acetone solvate was obtained as pale yellowish prisms.
Yield: 88.4%
mp: 223°–226° C. (from acetone-isopropyl ether)
Elemental analysis for $C_{30}H_{27}ClN_2O_5 \cdot \frac{1}{2}(CH_3)_2CO$ Calculated: C 67.66; H 5.31; N 5.09 Found : C 67.54; H 5.42; N 4.79

EXAMPLE 56

By the same method as in Example 33, 4-(2-chlorophenyl)-6,7-dimethyl-3-(4-hydroxy-3,5-dimethoxycinnamoylamino) quinoline was obtained as pale yellowish prisms.
Yield: 89.9%
mp: 278°–280° C. (from ethanol-chloroform)
Elemental analysis for $C_{28}H_{25}ClN_2O_4$ Calculated: C 68.78; H 5.15; N 5.73 Found : C 68.53; H 5.25; N 5.53

EXAMPLE 57

To a mixture of 4-acetoxy-3,5-dimethoxycinnamic acid (319 mg), dimethylformamide (one drop) and tetrahydrofuran (4 ml) was dropwise added oxalyl chloride (0.16 ml). The mixture was then stirred for 30 minutes at room temperature. The solvent was removed and the residue was dissolved in dichloromethane (4 ml), to which 3-amino-6,8-dimethyl-4-(4-fluorophenyl)quinoline (266 mg) and N,N-dimethylaniline (0.13 ml) were added. The resultant solution was stirred for 6 hours at room temperature, washed with water and dried (MgSO$_4$). Thereafter, the solvent was removed and the residue was crystallized from ethanol (509 mg, 99.0%). The obtained crystals were recrystallized from acetone-hexane to give 3-(4-acetoxy-3,5-dimethoxycinnamoylamino)-6,8-dimethyl-4-(4-fluorophenyl)quinoline as colorless needles.
mp: 260°–261° C.
Elemental analysis for $C_{30}H_{27}FN_2O_5$ Calculated: C 70.03; H 5.29; N 5.44 Found : C 69.66; H 5.16; N 5.37

EXAMPLE 58

By the same method as in Example 57, 3-(4-acetoxy-3,5-dimethoxycinnamoylamino)-6,8-dimethyl-4-(2-fluorophenyl)quinoline hydrochloride hydrate was obtained as colorless needles.
Yield: 40.9%
mp: 168°–169° C. (from acetone)
Elemental analysis for $C_{30}H_{27}FN_2O_5 \cdot HCl \cdot H_2O$ Calculated: C 63.32; H 5.31; N 4.92 Found : C 63.32; H 5.35; N 4.82

EXAMPLE 59

By the same method as in Example 33, 4-(2-chlorophenyl)-3-(4-hydroxy-3,5-dimethoxycinnamoylamino)-6-methylquinoline was obtained as pale yellowish needles.
Yield: 89.5%
mp: 235°–236° C. (from acetone)
Elemental analysis for $C_{27}H_{23}ClN_2O_4$ Calculated: C 68.28; H 4.88; N 5.90 Found : C 67.97; H 5.18; N 5.55

EXAMPLE 60

By the same method as in Example 57, 3-(4-acetoxy-3,5-dimethoxycinnamoylamino)-6-methyl-4-(2-methylphenyl)quinoline was obtained as pale yellowish prisms.
Yield: 54.8%
mp: 242°–243° C. (from acetone)
Elemental analysis for $C_{30}H_{28}N_2O_5$ Calculated: C 72.56; H 5.68; N 5.64 Found : C 72.41; H 5.85; N 5.50

EXAMPLE 61

By the same method as in Example 57, 3-(4-acetoxy-3,5-dimethoxycinnamoylamino)-4-(3,4-dimethoxyphenyl)-6-methylquinoline hydrate was obtained as pale yellowish prisms.
Yield: 68.1%
mp: 258°–261° C. (from ethanol-chloroform)
Elemental analysis for $C_{31}H_{30}N_2O_7 \cdot H_2O$ Calculated: C 66.41; H 5.75; N 5.00 Found : C 66.42; H 5.53; N 4.84

EXAMPLE 62

By the same method as in Example 57, 3-(4-acetoxy-3,5-dimethoxycinnamoylamino)-7-chloro-8-methyl-4-(2-methylphenyl)quinoline was obtained as pale yellowish prisms.
Yield: 53.7%
mp: 213°–214° C. (from acetone-isopropyl ether)
Elemental analysis for $C_{30}H_{27}ClN_2O_5$ Calculated: C 67.86; H 5.13; N 5.28 Found : C 67.85; H 5.31; N 5.08

EXAMPLE 63

By the same method as in Example 57, 3-(4-acetoxy-3,5-dimethoxycinnamoylamino)-6-chloro-4-(2-methylphenyl)quinoline was obtained as colorless prisms.
Yield: 62.0%
mp: 277°–278° C. (from acetone)
Elemental analysis for $C_{29}H_{25}ClN_2O_5$ Calculated: C 67.38; H 4.87; N 5.42 Found : C 67.41; H 4.88; N 5.42

EXAMPLE 64

By the same method as in Example 57, 3-(4-acetoxy-3,5-dimethoxycinnamoylamino)-6-methoxy-4-phenylquinoline was obtained as colorless prisms.
Yield: 83.0%
mp: 273°–275° C. (from acetone)
Elemental analysis for $C_{29}H_{26}N_2O_6$ Calculated: C 69.87; H 5.26; N 5.62 Found : C 69.55; H 5.24; N 5.46

EXAMPLE 65

By the same method as in Example 57, 3-(4-acetoxy-3,5-dimethoxycinnamoylamino)-6,7-dimethoxy-4-phenylquinoline was obtained as colorless needles.
Yield: 58.0%
mp: 256°–257° C. (from acetone)
Elemental analysis for $C_{30}H_{28}N_2O_7$ Calculated: C 68.17; H 5.34; N 5.30 Found : C 68.44; H 5.36; N 5.20

EXAMPLE 66

By the same method as in Example 57, 3-(4-acetoxy-3,5-dimethoxycinnamoylamino)-8-chloro-4-(2-chlorophenyl)-6-methylquinoline hydrate was obtained as colorless prisms.
Yield: 85.2%
mp: 147°–150° C. (from acetone-water)

Elemental analysis for $C_{29}H_{24}Cl_2N_2O_5 \cdot 2\frac{1}{2}H_2O$ Calculated: C 58.40; H 4.90; N 4.70 Found : C 58.25; H 4.67; N 4.60

EXAMPLE 67

To a solution of 4-(2-chlorophenyl)-3-(4-hydroxy-3,5-dimethoxycinnamoyl)-6,8-dimethylquinoline ethanol solvate (535 mg) in pyridine solution (3 ml) was added propionic anhydride (260 mg). The resultant solution was stirred for 3 hours at room temperature, diluted with water and then, extracted with ethyl acetate. The ethyl acetate layer was washed with water and dried (MgSO$_4$) . The solvent was removed and the residue was crystallized from acetone-hexane to give 4-(2-chlorophenyl)-3-(3,5-dimethoxy-4-propionyloxycinnamoylamino)-6,8-dimethylquinoline (503 mg, 92.3%). The obtained crystals were recrystallized from acetone-hexane to give colorless needles.

mp: 235°-236° C.

Elemental analysis for $C_{31}H_{29}ClN_2O_5$ Calculated: C 68.32; H 5.36; N 5.14 Found : C 68.22; H 5.63; N 5.09

EXAMPLE 68

To a mixture of 4-(2-chlorophenyl)-3-(4-hydroxy-3,5-dimethoxycinnamoyl)-6,8-dimethylquinoline ethanol solvate (535 mg), triethylamine (0.14 ml) and dichloromethane (5 ml) was dropwise added ethyl chlorocarbonate (0.1 ml). The mixture was stirred for 15 minutes at room temperature, then, washed with water and dried (MgSO$_4$). The solvent was removed and the residue was crystallized from ethanol to give 4-(2-chlorophenyl)-3-(4-ethoxycarbonyloxy-3,5-dimethoxycinnamoylamino)-6,8-dimethylquinoline (532 mg, 94.8%). The obtained crystals were recrystallized from acetone-hexane to give colorless prisms.

mp: 228°-229° C.

Elemental analysis for $C_{31}H_{29}ClN_2O_6$ Calculated: C 66.37; H 5.21; N 4.99 Found : C 66.52; H 5.24; N 4.93

EXAMPLE 69

To a solution of 4-(2-chlorophenyl)-3-(4-hydroxy-3,5-dimethoxycinnamoylamino)-6,8-dimethylquinoline ethanol solvate (535 mg) in pyridine (3 ml) was dropwise added dimethylcarbamoyl chloride (0.28 ml), followed by standing for one night at room temperature. The mixture was then diluted with water and extracted with ethyl acetate. The ethyl acetate layer was washed with water and dried (MgSO$_4$). The solvent was removed and the residue was crystallized from isopropyl ether to give 4-(2-chlorophenyl)-3-(3,5-dimethoxy-4-dimethylcarbamoyloxycinnamoyl)-6,8-dimethylquinoline (536 mg, 95.7%). The obtained crystals were recrystallized from acetone to give colorless needles.

mp: 240°-241° C.

Elemental analysis for $C_{31}H_{30}ClN_3O_5$ Calculated: C 66.48; H 5.40; N 7.50 Found : C 66.23; H 5.21; N 7.39

EXAMPLE 70

By the same method as in Example 57, 3-(4-acetoxy-3,5-dimethoxycinnamoylamino)-4-(2-chlorophenyl)-2,6,8-trimethylquinoline was obtained.

Yield: 66.4% mp: 225°-226° C. (from acetone)

Elemental analysis for $C_{31}H_{29}Cl_2N_2O_5$ Calculated: C 68.32; H 5.36; N 5.14 Found : C 68.11; H 5.35; N 5.08

EXAMPLE 71

By the same method as in Example 57, 3-(4-acetoxy-3,5-dimethoxycinnamoylamino)-4-(2-chlorophenyl)-6,8-dimethyl-2-methoxyquinoline was obtained.

Yield: 65.4% mp: 230°-231° C. (from acetone-hexane)

Elemental analysis for $C_{31}H_{29}ClN_2O_6$ Calculated: C 66.37; H 5.21; N 4.99 Found : C 66.29; H 5.30; N 4.93

EXAMPLE 72

By the same method as in Example 57, 3-(4-acetoxy-3,5-dimethoxycinnamoylamino)-4-(2-bromophenyl)-6-methylquinoline was obtained.

Yield: 35.1% mp: 238°-240° C. (from acetone-hexane)

Elemental analysis for $C_{29}H_{25}BrN_2O_5$ Calculated: C 62.04; H 4.49; N 4.99 Found : C 61.74; H 4.63; N 4.71

We claim:

1. A method for treatment of hypercholesterolemia or atherosclerosis, which comprises administration to a mammal in need thereof of an effective amount of a quinoline derivative having the following formula:

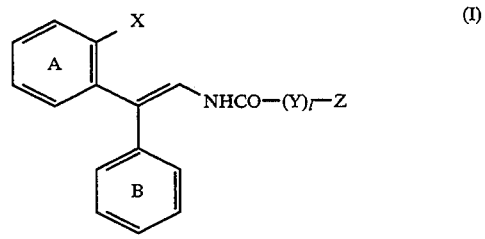

wherein each phenyl ring of A and B can have one or more substituents; X is

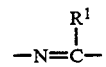

($R^1$ is a hydrogen atom, a lower alkyl group or a lower alkoxy group) or

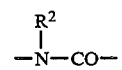

($R^2$ is a hydrogen atom or a lower alkyl group); Y is —(CH$_2$)$_m$— (m is 0, 1 or 2) or —CH=CH—; Z is a group of the formula:

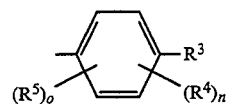

wherein $R^3$ and $R^4$ are each a hydrogen or halogen atom, or a lower alkyl, lower alkoxy, lower acyloxy, lower alkoxycarbonyloxy, N,N-di-lower alkylcarbamoyloxy, optionally esterified carboxy or hydroxyl group, $R^5$ is a halogen atom, or a lower alkyl, lower alkoxy, lower acyloxy, lower alkoxycarbonyloxy, N,N-di-lower alkylcarbamoyloxy, optionally esterified carboxy or hydroxyl group, and n and o are each 1 or 2; l is 0 or 1, or its pharmaceutically acceptable salt.

2. A method for inhibiting acyl-CoA:cholesterolacyltransferase which comprises administration to a mammal in need thereof of an effective amount of a quinoline derivative having the following formula:

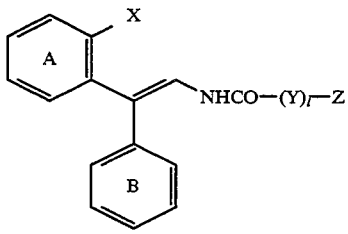

wherein each phenyl ring of A and B can have one or more substituents; X is

($R^1$ is a hydrogen atom, a lower alkyl group or a lower alkoxy group) or $$-\overset{R^2}{\underset{|}{N}}-CO-$$

($R^2$ is a hydrogen atom or a lower alkyl group); Y is —$(CH_2)_m$—(m is 0, 1 or 2) or —CH=CH—; Z is a group of the formula:

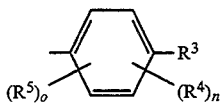

wherein $R^3$ and $R^4$ are each a hydrogen or halogen atom, or a lower alkyl, lower alkoxy, lower acyloxy, lower alkoxycarbonyloxy, N,N-di-lower alkylcarbamoyloxy, optionally esterified carboxy or hydrogen group, $R^5$ is a halogen atom, or a lower alkyl lower alkoxy, lower acyloxy, lower alkoxycarbonyloxy, N,N-di-lower alkylcarbamoyloxy, optionally esterified carboxy or hydroxyl group, and n and o are each 1 or 2; l is 0 or 1, or its pharmaceutically acceptable salt.

3. The method of claim 1, wherein the phenyl Z group has two to four substituents.

4. The method of claim 2, wherein the phenyl Z group has two to four substituents.

* * * * *

UNITED STATES PATENT AND TRADEMARK OFFICE
CERTIFICATE OF CORRECTION

PATENT NO. : 5,362,742
DATED : November 8, 1994
INVENTOR(S) : MEGURO et al.

It is certified that error appears in the above-indentified patent and that said Letters Patent is hereby corrected as shown below:

In the abstract, line 2, compound (I) should appear as shown below:

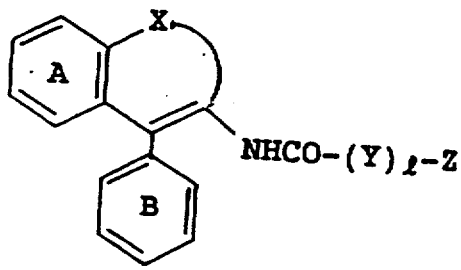

Column 1, line 50, compound (I) should appear as shown below:

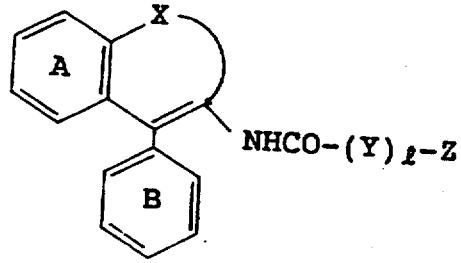

UNITED STATES PATENT AND TRADEMARK OFFICE
CERTIFICATE OF CORRECTION

PATENT NO. : 5,362,742
DATED : November 8, 1994
INVENTOR(S) : MEGURO et al.

Page 2 of 6

It is certified that error appears in the above-indentified patent and that said Letters Patent is hereby corrected as shown below:

Column 4, line 20, compound (II), a binding arch should appear as shown below:

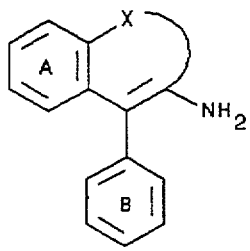

line 55, compound (IV), a binding arch should appear as shown below:

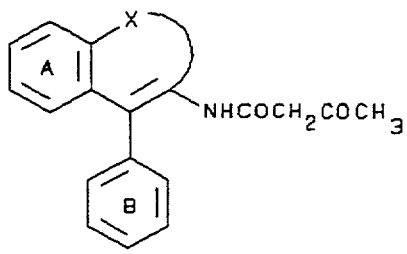

UNITED STATES PATENT AND TRADEMARK OFFICE
CERTIFICATE OF CORRECTION

PATENT NO. : 5,362,742
DATED : November 8, 1994
INVENTOR(S) : MEGURO et al.

It is certified that error appears in the above-indentified patent and that said Letters Patent is hereby corrected as shown below:

Column 10, line 5, compound (XI), a binding arch should appear as shown below:

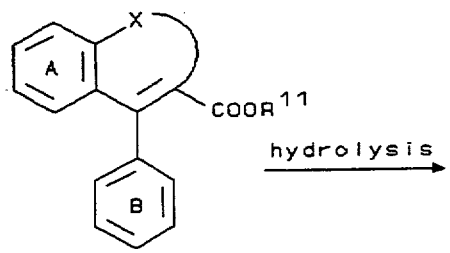

line 16, compound (XII), a binding arch should appear as shown below:

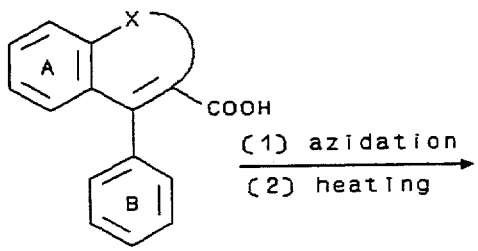

UNITED STATES PATENT AND TRADEMARK OFFICE
CERTIFICATE OF CORRECTION

PATENT NO. : 5,362,742
DATED : November 8, 1994
INVENTOR(S) : MEGURO et al.

It is certified that error appears in the above-indentified patent and that said Letters Patent is hereby corrected as shown below:

line 27, compound (XIII), a binding arch should appear as shown below:

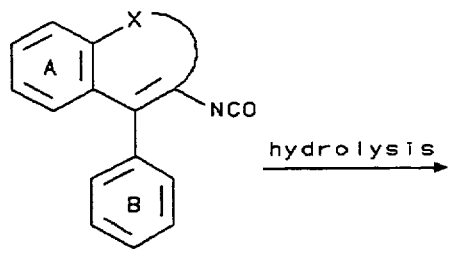

line 38, compound (II), a binding arch should appear as shown below:

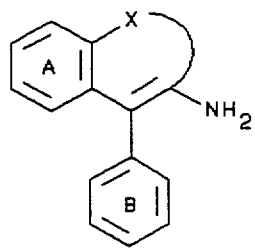

UNITED STATES PATENT AND TRADEMARK OFFICE
CERTIFICATE OF CORRECTION

PATENT NO. : 5,362,742
DATED : November 8, 1994
INVENTOR(S) : MEGURO et al.

It is certified that error appears in the above-indentified patent and that said Letters Patent is hereby corrected as shown below:

Column 32, claim 1, compound (I) should appear as shown below:

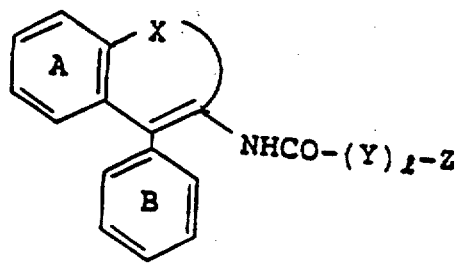

UNITED STATES PATENT AND TRADEMARK OFFICE
CERTIFICATE OF CORRECTION

PATENT NO. : 5,362,742
DATED : November 8, 1994
INVENTOR(S) : MEGURO et al.

It is certified that error appears in the above-indentified patent and that said Letters Patent is hereby corrected as shown below:

Column 33, claim 2, compound (I) should appear as shown below:

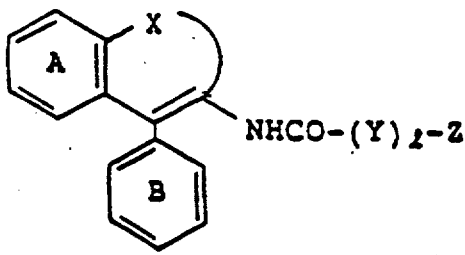

Signed and Sealed this

Twenty-sixth Day of March, 1996

Attest:

BRUCE LEHMAN

Attesting Officer  Commissioner of Patents and Trademarks